US009987427B1

(12) United States Patent
Polsky et al.

(10) Patent No.: US 9,987,427 B1
(45) Date of Patent: Jun. 5, 2018

(54) DIAGNOSTIC/DRUG DELIVERY "SENSE-RESPOND" DEVICES, SYSTEMS, AND USES THEREOF

(71) Applicant: Sandia Corporation, Albuquerque, NM (US)

(72) Inventors: Ronen Polsky, Albuquerque, NM (US); Philip Rocco Miller, Albuquerque, NM (US); Thayne L. Edwards, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 169 days.

(21) Appl. No.: 14/746,301

(22) Filed: Jun. 22, 2015

Related U.S. Application Data

(60) Provisional application No. 62/016,343, filed on Jun. 24, 2014.

(51) Int. Cl.
| | | |
|---|---|---|
| *A61M 5/172* | (2006.01) | |
| *A61B 10/00* | (2006.01) | |
| *A61B 5/145* | (2006.01) | |
| *A61M 37/00* | (2006.01) | |
| *A61B 5/157* | (2006.01) | |

(52) U.S. Cl.
CPC ........... *A61M 5/1723* (2013.01); *A61B 5/157* (2013.01); *A61M 37/0015* (2013.01); *A61M 2005/1726* (2013.01); *A61M 2037/0023* (2013.01); *A61M 2037/0061* (2013.01); *A61M 2202/048* (2013.01); *A61M 2202/30* (2013.01)

(58) Field of Classification Search
CPC ...... A61M 2037/0023; A61M 37/0015; A61M 2037/0046; A61M 2205/3303; A61M 5/1723; A61M 2005/1726; A61B 5/00; A61B 10/00; A61B 10/008; A61B 10/02; A61B 5/157; A61B 5/145
See application file for complete search history.

(56) References Cited

U.S. PATENT DOCUMENTS

| | | |
|---|---|---|
| 5,217,112 A | 6/1993 | Almon |
| 6,132,755 A | 10/2000 | Eicher et al. |
| 6,251,595 B1 | 6/2001 | Gordon et al. |
| 6,281,006 B1 | 8/2001 | Heller et al. |
| 6,398,931 B1 | 6/2002 | Burchette et al. |
| 6,443,179 B1 | 9/2002 | Benavides et al. |

(Continued)

FOREIGN PATENT DOCUMENTS

| | | |
|---|---|---|
| WO | WO 2006/060106 A1 | 6/2006 |
| WO | WO 2006/116242 A2 | 11/2006 |

(Continued)

OTHER PUBLICATIONS

U.S. Appl. No. 14/538,096, filed Nov. 11, 2014, Polsky et al.
(Continued)

*Primary Examiner* — Quynh-Nhu H Vu
(74) *Attorney, Agent, or Firm* — Helen S. Baca

(57) ABSTRACT

The present invention is directed to devices, systems, and methods for detecting and/or monitoring one or more markers in a sample. In particular, such devices integrate a plurality of hollow needles configured to extract or obtain a fluid sample from a subject, as well as transducers to detect a marker of interest.

22 Claims, 2 Drawing Sheets

(56) References Cited

U.S. PATENT DOCUMENTS

| | | | |
|---|---|---|---|
| 6,548,895 B1 | 4/2003 | Benavides et al. | |
| 6,652,720 B1 | 11/2003 | Mansouri et al. | |
| 6,908,453 B2 | 6/2005 | Fleming et al. | |
| 7,250,147 B2 | 7/2007 | Tour et al. | |
| 7,314,505 B1 | 1/2008 | Wheeler et al. | |
| 7,344,499 B1* | 3/2008 | Prausnitz | A61M 37/0015 600/309 |
| 7,550,071 B1 | 6/2009 | Dirk et al. | |
| 7,736,484 B2 | 6/2010 | Bureau et al. | |
| 8,349,547 B1 | 1/2013 | Burckel et al. | |
| 9,157,161 B1 | 10/2015 | Brozik et al. | |
| 9,212,430 B1 | 12/2015 | Harper et al. | |
| 9,533,887 B1 | 1/2017 | Polsky et al. | |
| 9,737,247 B2 | 8/2017 | Wang et al. | |
| 9,743,870 B2 | 8/2017 | Wang et al. | |
| 2003/0199812 A1* | 10/2003 | Rosenberg | A61B 17/205 604/47 |
| 2004/0176732 A1* | 9/2004 | Frazier | A61M 37/0015 604/345 |
| 2004/0248428 A1 | 12/2004 | Bureau et al. | |
| 2005/0107742 A1* | 5/2005 | Ghovanloo | A61M 37/0015 604/117 |
| 2006/0025717 A1* | 2/2006 | Zimmermann | A61M 37/0015 604/46 |
| 2006/0264779 A1* | 11/2006 | Kemp | A61B 5/1411 600/583 |
| 2007/0158212 A1 | 7/2007 | Filanovsky | |
| 2008/0221408 A1* | 9/2008 | Hoarau | A61B 5/0059 600/310 |
| 2009/0187167 A1* | 7/2009 | Sexton | A61B 17/205 604/891.1 |
| 2010/0000881 A1 | 1/2010 | Franzen et al. | |
| 2010/0036336 A1* | 2/2010 | Bogdanova | A61F 13/64 604/361 |
| 2011/0105871 A1 | 5/2011 | Zimmermann et al. | |
| 2011/0224515 A1 | 9/2011 | Mir et al. | |
| 2012/0245445 A1* | 9/2012 | Black | A61B 5/1468 600/365 |
| 2013/0306155 A1 | 11/2013 | Mathus et al. | |
| 2014/0336487 A1 | 11/2014 | Wang et al. | |

FOREIGN PATENT DOCUMENTS

| | | | |
|---|---|---|---|
| WO | WO 2010/022252 A2 | 2/2010 | |
| WO | WO 2013/058879 A2 | 4/2013 | |
| WO | WO2013058879 | * 4/2013 | A61M 37/00 |

OTHER PUBLICATIONS

U.S. Appl. No. 15/078,870, filed Mar. 23, 2016, Polsky et al.
Arrigan DWM, "Nanoelectrodes, nanoelectrode arrays and their applications," *Analyst* 2004;129:1157-65.
Bakker E et al., "Carrier-based ion-selective electrodes and bulk optodes. 1. General characteristics," *Chem. Rev.* 1997; 97:3083-132.
Bravo R et al., "Possibilities and limitations in miniaturized sensor design for uric acid," *Analyst* Jul. 1998;123(7):1625-30.
Brown MB et al., "Dermal and transdermal drug delivery systems: current and future prospects," *Drug Deilv.* May-Jun. 2006;13(3):175-87.
Burckel DB et al., "Lithographically defined porous carbon electrodes," *Small* 2009;5:2792-6.
Ceyssens F et al., "Fabrication process for tall, sharp, hollow, high aspect ratio polymer microneedles on a platform," *J. Micromech. Microeng.* 2013;23(7):075023 (7 pages).
Chakraborty S et al., "Mediated electrocatalytic oxidation of bioanalytes and biosensing of glutamate using functionalized multiwall carbon nanotubes-biopolymer nanocomposite," *J. Electroanal. Chem.* 2007;609(2):155-62.
Chaudhuri BP et al., "A novel method for monolithic fabrication of polymer microneedles on a platform for transdermal drug delivery," *Conf. Proc. IEEE Eng. Med. Biol. Soc.* 2013;2013:156-9.

Choi JW et al., "Insertion force estimation of various microneedle array-type structures fabricated by a microstereolithography apparatus," *Int'l Joint Conference SICE-ICASE*, held on Oct. 18-21, 2006 in Busan, South Korea (pp. 3678-3681).
Chua B et al., "Effect of microneedles shape on skin penetration and minimally invasive continuous glucose monitoring in vivo," *Sens. Actuat. A* 2013;203:373-81.
Coffey JW et al., "Early circulating biomarker detection using a wearable microprojection array skin patch," *Biomaterials* Dec. 2013;34(37):9572-83.
Corrie SR et al., "Surface-modified microprojection arrays for intradermal biomarker capture, with low non-specific protein binding," *Lab on a Chip* 2010;10(20):2655-8.
Crespo GA et al., "Ion-selective electrodes using carbon nanotubes as ion-to-electron transducers," *Anal. Chem.* 2008;80:1316-22.
Dagdeviren C et al., "Conformal piezoelectric energy harvesting and storage from motions of the heart, lung, and diaphragm," *Proc. Nat'l Acad. Sci. USA* Feb. 4, 2014;111(5):1927-32.
Davidson A et al., "Transdermal drug delivery by coated microneedles: Geometry effects on effective skin thickness and drug permeability," *Chem. Eng. Res. Design* 2008;86(11):1196-206.
Davis SP et al., "Hollow metal microneedles for insulin delivery to diabetic rats," *IEEE Trans. Biomed. Eng.* May 2005;52(5):909-15.
Davis SP et al., "Insertion of microneedles into skin: measurement and prediction of insertion force and needle fracture force," *J. Biomech.* Aug. 2004;37(8):1155-63.
Donnelly RF et al., "Design, optimization and characterisation of polymeric microneedle arrays prepared by a novel laser-based micromoulding technique," *Pharm. Res.* Jan. 2011;28(1):41-57.
Donnelly RF et al., "Hydrogel-forming microneedles increase in volume during swelling in skin, but skin barrier function recovery is unaffected," *J. Pharm. Sci.* May 2014;103(5):1478-86 (Abstract, 3 pages).
Downard AJ et al., "Covalent modification of carbon electrodes for voltammetric differentiation of dopamine and ascorbic acid," *Anal. Chim. Acta* 1995;317(1-3):303-10.
Edwards TL et al., "A parallel microfluidic channel fixture fabricated using laser ablated plastic laminates for electrochemical and chemiluminescent biodetection of DNA," *Biomicrofluidics* Dec. 2011;5(4):Article 044115 (14 pages).
Ei-Laboudi A et al., "Use of microneedle array devices for continuous glucose monitoring: a review," *Diabetes Technol. Therap.* 2013;15:101-15.
Forvi E et al., "Preliminary technological assessment of microneedles-based dry electrodes for biopotential monitoring in clinical examinations," *Sens. Actuat. A* 2012;180:177-86.
Garcia A et al., "Dexcom G4AP: an advanced continuous glucose monitor for the artificial pancreas," *J. Diabetes Sci. Technol.* Nov. 1, 2013;7(6):1436-45.
Gardeniers HJGE et al., "Silicon micromachined hollow microneedles for transdermal liquid transport," *J. Microelectromech. Sys.* 2003;12(6):855-62.
Gatzoulis L et al., "Wearable and portable eHealth systems. Technological issues and opportunities for personalized care," *IEEE Eng. Med. Biol. Mag.* Sep.-Oct. 2007;26(5):51-6.
Gill HS et al., "Coated microneedles for transdermal delivery," *J. Control. Release* Feb. 12, 2007;117(2):227-37.
Gill HS et al., "Effect of microneedle design on pain in human volunteers," *Clin. J. Pain* Sep. 2008;24(7):585-94.
Gittard SD et al., "Fabrication of microscale medical devices by two-photon polymerization with multiple foci via a spatial light modulator," *Biomed. Opt. Express* Nov. 1, 2011;2(11):3167-78.
Gittard SD et al., "Fabrication of polymer microneedles using a two-photon polymerization and micromolding process," *J. Diabetes Sci. Technol.* 2009;3:304-11.
Gittard SD et al., "Multiphoton microscopy of transdermal quantum dot delivery using two photon polymerization-fabricated polymer microneedles," *Faraday Discuss.* 2011;149:171-85.
Gittard SD et al., "Two photon polymerization of microneedles for transdermal drug delivery," *Exp. Opin. Drug Deliv.* 2010;7(4):513-33.

(56) References Cited

OTHER PUBLICATIONS

Gooding JJ, "Advances in interfacial design for electrochemical biosensors and sensors: aryl diazonium salts for modifying carbon and metal electrodes," *Electroanal.* 2008;20(6):573-82.

Gubala V et al., "Point of care diagnostics: Status and future," *Anal. Chem.* 2012;84(2):487-515.

Harper JC et al., "A multifunctional thin film Au electrode surface formed by consecutive electrochemical reduction of aryl diazonium salts," *Langmuir* 2009;25:3282-8.

Harper JC et al., "Maleimide-activated aryl diazonium salts for electrode surface functionalization with biological and redox-active molecules," *Langmuir* Mar. 4, 2008;24(5):2206-11.

Harper JC et al., "Selective immobilization of DNA and antibody probes on electrode arrays: simultaneous electrochemical detection of DNA and protein on a single platform," *Langmuir* Jul. 31, 2007;23(16):8285-7.

Hart JP et al., "Some recent designs and developments of screen-printed carbon electrochemical sensors/biosensors for biomedical, environmental, and industrial analyses," *Anal. Lett.* 2005;37(5):789-830.

Helen ML et al., "Overoxidation of carbon-fiber microelectrodes enhances dopamine adsorption and increases sensitivity," *Analyst* Dec. 2003;128(12):1413-9.

Henry S et al., "Microfabricated microneedles: a novel approach to transdermal drug delivery," *J. Pharm. Sci.* Aug. 1998;87(8):922-5.

Invernale MA et al., "Microneedle electrodes toward an amperometric glucose-sensing smart patch," *Adv. Healthcare Mater.* 2014;3(3):338-42.

Jacobs CB et al., "Review: Carbon nanotube based electrochemical sensors for biomolecules," *Anal. Chim. Acta* Mar. 10, 2010;662(2):105-27.

Jia W et al., "Electrochemical tattoo biosensors for real-time non-invasive lactate monitoring in human perspiration," *Anal. Chem.* 2013;85:6553-60.

Jin J et al., "Chitin microneedles for an easy-to-use tuberculosis skin test," *Adv. Healthc. Mater.* Mar. 2014;3(3):349-53 (Abstract, 3 pages).

Jina A et al., "Design, development, and evaluation of a novel microneedle array-based continuous glucose monitor," *J. Diabetes Sci. Technol.* May 2014;8(3):483-7.

Justino CIL et al., "Review of analytical figures of merit of sensors and biosensors in clinical applications," *Trends Analyt. Chem.* 2010;29:1172-83.

Kaushik S et al., "Lack of pain associated with microfabricated microneedles," *Anesth. Analg.* Feb. 2001;92(2):502-4.

Keum do H et al., "Microneedle biosensor for real-time electrical detection of nitric oxide for in situ cancer diagnosis during endomicroscopy," *Adv. Healthc. Mater.* Jun. 2015;4(8):1153-8 (Abstract, 3 pages).

Kim DH et al., "Epidermal electronics," *Science* 2011;333:838-43.

Kim K et al., "A tapered hollow metallic microneedle array using backside exposure of SU-8," *J. Micromech. Microeng.* 2004;14(4):597-603.

Kim YC et al., "Microneedles for drug and vaccine delivery," *Adv. Drug Deliv. Rev.* 2012;64:1547-68.

Lai C et al., "Ion-selective electrodes with three-dimensionally ordered macroporous carbon as the solid contact," *Anal. Chem.* 2007;79:4621-6.

Lee BS et al., "A fully automated immunoassay from whole blood on a disc," *Lab Chip* Jun. 7, 2009;9(11):1548-55.

Lee KT et al., "Capture of the circulating *Plasmodium falciparum* biomarker HRP2 in a multiplexed format, via a wearable skin patch," *Anal. Chem.* Oct. 21, 2014;86(20):10474-83.

Li CG et al., "An optimized hollow microneedle for minimally invasive blood extraction," *Biomed. Microdevices* Feb. 2013;15(1):17-25.

Li F et al., "All-solid-state potassium-selective electrode using graphene as the solid Contact," *Analyst* 2012;137:618-23.

Li X et al., "Experimental study on neuroendocrinological and immunological characteristics of the military-trained artillerymen," *Chin. Med. J. (Engl.)* Apr. 2012;125(7):1292-6.

Mang A et al., "Biocompatibility of an electrochemical sensor for continuous glucose monitoring in subcutaneous tissue," *Diabetes Technol. Ther.* Feb. 2005;7(1):163-73.

Martanto W et al., "Mechanism of fluid infusion during microneedle insertion and retraction," *J. Controlled Release* 2006;112(3):357-61.

Martanto W et al., "Microinfusion using hollow microneedles," *Pharm. Res.* Jan. 2006;23(1):104-13.

Mastrototaro JJ, "The MiniMed continuous glucose monitoring system," *Diabetes Technol. Ther.* 2000;2 Suppl 1:S13-8.

Matteucci M et al., "Poly vinyl alcohol re-usable masters for microneedle replication," *Microelectron. Eng.* 2009;86(4-6):752-6.

McAllister DV et al., "Microfabricated microneedles for gene and drug delivery," *Annu. Rev. Biomed. Eng.* 2000;2:289-313.

McAllister DV et al., "Microfabricated needles for transdermal delivery of macromolecules and nanoparticles: fabrication methods and transport studies," *Proc. Nat'l Acad. Sci. USA* Nov. 25, 2003;100(24):13755-60.

McCreery RL, "Advanced carbon electrode materials for molecular electrochemistry," *Chem. Rev.* Jul. 2008;108(7):2646-87.

Miller PR et al., "Hollow microneedle-based sensor for multiplexed transdermal electrochemical sensing," *J. Vis. Exp.* Jun. 1, 2012;(64):e4067 (6 pages).

Miller PR et al., "Integrated carbon fiber electrodes within hollow polymer microneedles for transdermal electrochemical sensing," *Biomicrofluidics* 2011;5:013415 (14 pages).

Miller PR et al., "Microneedle-based transdermal sensor for on-chip potentiometric determination of K+," *Adv. Healthcare Mater.* 2014;3(6):876-81.

Miller PR et al., "Multiplexed microneedle-based biosensor array for characterization of metabolic acidosis," *Talanta* 2012;88:739-42.

Mukerjee EV et al., "Microneedle array for transdermal biological fluid extraction and in situ analysis," *Sens. Actuat. A* 2004;114(2):267-75.

Muller DA et al., "Surface modified microprojection arrays for the selective extraction of the Dengue Virus NS1 protein as a marker for disease," *Anal. Chem.* 2012;84:3262-8.

Narayan RJ et al., "Medical prototyping using two photon polymerization," *Mater. Today* 2010;13(12):42-8.

Nayak A et al., "Potential of biodegradable microneedles as a transdermal delivery vehicle for lidocaine," *Biotechnol. Lett.* Sep. 2013;35(9):1351-63.

Norman JJ et al., "Hollow microneedles for intradermal injection fabricated by sacrificial micromolding and selective electrodeposition," *Biomed. Microdevices.* Apr. 2013;15(2):203-10.

Olatunji O et al., "Influence of array interspacing on the force required for successful microneedle skin penetration: theoretical and practical approaches," *J. Pharm. Sci.* 2013;102(4):1209-21.

Ovsianikov A et al., "Two photon polymerization of polymer-ceramic hybrid materials for transdermal drug delivery," *Int'l J. Appl. Ceram. Technol.* 2007;4(1):22-9.

Paik SJ et al., "In-plane single-crystal-silicon microneedles for minimally invasive microfluid systems," *Sens. Actuat. A* 2004;114(2-3):276-84.

Papadea C et al., "Evaluation of the i-STAT Portable Clinical Analyzer for point-of-care blood testing in the intensive care units of a university children's hospital," *Ann. Clin. Lab. Sci.* 2002 Summer;32(3):231-43.

Park JH et al., "Biodegradable polymer microneedles: fabrication, mechanics and transdermal drug delivery," *J. Control. Release* May 5, 2005;104(1):51-66.

Park JH et al., "Tapered conical polymer microneedles fabricated using an integrated lens technique for transdermal drug delivery," *IEEE Trans. Biomed. Eng.* May 2007;54(5):903-13.

Pérennès F et al., "Sharp beveled tip hollow microneedle arrays fabricated by LIGA and 3D soft lithography with polyvinyl alcohol," *J. Micromech. Microeng.* 2006;16(3):473-9.

(56) References Cited

OTHER PUBLICATIONS

Ping J et al., "Development of an all-solid-state potassium ion-selective electrode using graphene as the solid-contact transducer," *Electrochem. Commun.* 2011;13:1529-32.

Polsky R et al., "Diazonium-functionalized horseradish peroxidase immobilized via addressable electrodeposition: Direct electron transfer and electrochemical detection," *Langmuir* 2007;23:364-6.

Polsky R et al., "Electrically addressable cell immobilization using phenylboronic acid diazonium salts," *Angew. Chem. Int. Ed. Engl.* 2008;47(14):2631-4.

Polsky R et al., "Electrically addressable diazonium-functionalized antibodies for multianalyte electrochemical sensor applications," *Biosens. Bioelectron.* Jan. 18, 2008;23(6):757-64.

Polsky R et al., "Multifunctional electrode arrays: towards a universal detection platform," *Electroanalysis* 2008;20(6):671-9.

Polsky R et al., "Nucleic acid-functionalized Pt nanoparticles: catalytic labels for the amplified electrochemical detection of biomolecules," *Anal. Chem.* 2006;78:2268-71.

Polsky R et al., "Reagentless electrochemical immunoassay using electrocatalytic nanoparticle-modified antibodies," *Chem. Commun. (Camb.)* Jul. 14, 2007;(26):2741-3.

Prausnitz MR, "Microneedles for transdermal drug delivery," *Adv. Drug Deliv. Rev.* Mar. 27, 2004;56(5):581-7.

Pumera M, "Nanomaterials meet microfluidics," *Chem. Commun. (Camb.)* May 28, 2011;47(20):5671-80.

Purvis D et al., "Physiological and psychological fatigue in extreme conditions: overtraining and elite athletes," *PM&R* May 2010;2(5):442-50.

Raphael AP et al., "Targeted, needle-free vaccinations in skin using multilayered, densely-packed dissolving microprojection arrays," *Small* Aug. 16, 2010;6(16):1785-93.

Romanyuk AV et al., "Collection of analytes from microneedle patches," *Anal. Chem.* Nov. 4, 2014;86(21):10520-3.

Sakaguchi K et al., "A minimally invasive system for glucose area under the curve measurement using interstitial fluid extraction technology: evaluation of the accuracy and usefulness with oral glucose tolerance tests in subjects with and without diabetes," *Diabetes Technol. Ther.* Jun. 2012;14(6):485-91.

Shikida M et al., "Fabrication of a hollow needle structure by dicing, wet etching and metal deposition," *J. Micromech. Microeng.* 2006;16(10):2230-9.

Srinivasan V et al., "Clinical diagnostics on human whole blood, plasma, serum, urine, saliva, sweat, and tears on a digital microfluidic platform," *7th Int'l Conference on Miniaturized Chemical and Biochemical Analysis Systems*, held on Oct. 5-9, 2003 in Squaw Valley, CA (pp. 1287-1290).

Stett A et al., "Biological application of microelectrode arrays in drug discovery and basic research," *Anal. Bioanal. Chem.* Oct. 2003;377(3):486-95.

Stoeber B et al., "Arrays of hollow out-of-plane microneedles for drug delivery," *J. Microelectromech. Sys.* 2005;14(3):472-9.

Sullivan SP et al., "Dissolving polymer microneedle patches for influenza vaccination," *Nat. Med.* Aug. 2010;16(8):915-20.

Suzuki A et al., "Fabrication, characterization, and application of boron-doped diamond microelectrodes for in vivo dopamine detection," *Anal. Chem.* Nov. 15, 2007;79(22):8608-15.

Suzuki H et al., "A disposable "intelligent mosquito" with a reversible sampling mechanism using the volume-phase transition of a gel," *Sens. Actuat. B* 2002;83(1-3):53-9.

Tsuchiya K et al., "Development of blood extraction system for health monitoring system," *Biomed. Microdevices* Dec. 2005;7(4):347-53.

Vaddiraju S et al., "Emerging synergy between nanotechnology and implantable biosensors: a review," *Biosens. Bioelectron.* Mar. 15, 2010;25(7):1553-65.

Valdés-Ramírez G et al., "Microneedle-based self-powered glucose sensor," *Electrochem. Commun.* 2014;47:58-62.

Vazquez P et al., "Microscopic gel-liquid interfaces supported by hollow microneedle array for voltammetric drug detection," *Sens. Actuat. B* 2014;201:572-8.

Verbaan FJ et al., "Assembled microneedle arrays enhance the transport of compounds varying over a large range of molecular weight across human dermatomed skin," *J. Control. Release* Feb. 12, 2007;117(2):238-45.

Verbaan FJ et al., "Improved piercing of microneedle arrays in dermatomed human skin by an impact insertion method," *J. Control. Release* May 22, 2008;128(1):80-8.

Wang J et al., "Screen-printable sol-gel enzyme-containing carbon inks," *Anal. Chem.* Aug. 1996;68(15):2705-8.

Wang J, "Amperometric biosensors for clinical and therapeutic drug monitoring: a review," *J. Pharm. Biomed. Anal.* Feb. 1999;19(1-2):47-53.

Wang J, "Electrochemical biosensors: towards point-of-care cancer diagnostics," *Biosens. Bioelectron.* Apr. 15, 2006;21(10):1887-92.

Wang J, "Electrochemical glucose biosensors," *Chem. Rev.* Feb. 2008;108(2):814-25.

Wang PC et al., "Hollow polymer microneedle array fabricated by photolithography process combined with micromolding technique," *Annual Int'l Conference of the IEEE Engineering in Medicine and Biology Society*, held on Sep. 3-6, 2009 in Minneapolis, MN (pp. 7026-7029).

Wang PC et al., "Hypodermic-needle-like hollow polymer microneedle array using UV lithography into micromolds," *2011 IEEE 24th Int'l Conference on Micro Electro Mechanical Systems (MEMS)*, held on Jan. 23-27, 2011 in Cancun (pp. 1039-1042).

Wang PM et al., "Minimally invasive extraction of dermal interstitial fluid for glucose monitoring using microneedles," *Diabet. Technol. Therap.* 2005;7(1):131-41.

Wang PM et al., "Precise microinjection into skin using hollow microneedles," *J. Invest. Dermatol.* May 2006;126(5):1080-7.

Weeks SR et al., "Physiological and psychological fatigue in extreme conditions: the military example," *PM&R* May 2010;2(5):438-4.

Wilson GS et al., "Biosensors for real-time in vivo measurements," *Biosens. Bioelectron.* Jun. 15, 2005;20(12):2388-403.

Windmiller JR et al., "Bicomponent microneedle array biosensor for minimally-invasive glutamate monitoring," *Electroanalysis* 2011;23(10):2302-9.

Windmiller JR et al., "Microneedle array-based carbon paste amperometric sensors and biosensors," *Analyst* 2011;136:1846-51.

Windmiller JR et al., "Wearable electrochemical sensors and biosensors: A review," *Electroanalysis* 2013;25(1):29-46.

Wyatt FB et al., "The overtraining syndrome: A meta-analytic review," *J. Exerc. Physiol.* Apr. 2013 ;16(2):12-23.

Xiao X et al., "Lithographically defined three-dimensional graphene structures," *ACS Nano* 2012;6(4):3573-9.

Yang F et al., "A bubble-mediated intelligent microscale electrochemical device for single-step quantitative bioassays," *Adv. Mater.* Jul. 16, 2014;26(27):4671-6.

Yang SY et al., "A bio-inspired swellable microneedle adhesive for mechanical interlocking with tissue," *Nat. Commun.* 2013;4:1702 (10 pages).

Yeow B et al., "Surface modification and characterization of polycarbonate microdevices for capture of circulating biomarkers, both in vitro and in vivo," *Anal. Chem.* Nov. 5, 2013;85(21):10196-204.

Yu LM et al., A microfabricated electrode with hollow microneedles for ECG measurement, *Sens. Actuat. A* 2009;151(1):17-22.

Yung KL et al., "Sharp tipped plastic hollow microneedle array by microinjection moulding," *J. Micromech. Microeng.* 2012;22:015016 (10 pages).

Zahn JD et al., "Microdialysis microneedles for continuous medical monitoring," *Biomed. Microdevices* Mar. 2005;7(1):59-69.

Zhang L et al., "Integrated microcapillary for sample-to-answer nucleic acid pretreatment, amplification, and detection," *Anal. Chem.* Oct. 21, 2014;86(20):10461-6.

Zimmermann S et al., "A microneedle-based glucose monitor: fabricated on a wafer-level using in-device enzyme immobilization," *12th Int'l Conference on Transducers, Solid-State Sensors, Actuators and Microsystems*, held on Jun. 8-12, 2003 in Boston, MA (pp. 99-102, vol. 1).

\* cited by examiner

US 9,987,427 B1

DIAGNOSTIC/DRUG DELIVERY "SENSE-RESPOND" DEVICES, SYSTEMS, AND USES THEREOF

CROSS-REFERENCE TO RELATED APPLICATION

This application claims the benefit of U.S. Provisional Application No. 62/016,343, filed Jun. 24, 2014, which is hereby incorporated by reference in its entirety.

STATEMENT OF GOVERNMENT INTEREST

This invention was developed under Contract DE-AC04-94AL85000 between Sandia Corporation and the U.S. Department of Energy. The U.S. Government has certain rights in this invention.

FIELD OF THE INVENTION

The invention relates to methods and devices of electrochemical bioassay, and more particularly to miniaturizeable systems and their use for in vivo measurements. In particular embodiments, the invention provides an integrated, compact system to measure the systemic physiological state of an individual and to deliver one or more therapeutic agents, as needed, to the individual.

BACKGROUND OF THE INVENTION

Many conventional monitoring methods rely on macroscale systems that are undesirable due to requirements for large sample volumes, complicated fluid transfer between components, and the pain/tissue damage that can result from long-term device/human interactions. Microneedle-enabled analysis systems offer an ideal solution to all of these problems. Their size enables minimally-invasive interrogation due to their ability to puncture the skin's stratum corneum and access interstitial fluid without irritating deeper layers of the skin associated with pain, blood flow, or sensation.

The predominant use of these microneedles has been drug delivery, while little research exists on their usage for minimally invasive point-of-care sensing. No current forms of microneedles are capable of performing long-term sensing or providing drug-injection feedback loops as a sense-treat platform. One answer to this need would be an autonomous remote diagnostic device that is capable of interfacing with the human subject and performing a variety of diagnostic and treatment functions directed to that subject. The field is open for the development of such devices.

SUMMARY OF THE INVENTION

We have developed a microfluidic bioassay device that can be worn on an individual and can transdermally access a test sample (e.g., blood and/or interstitial fluid) to create a real-time long term autonomous diagnostic device to monitor physiological signatures. This device includes a needle, lancet, or puncturing tool, etc. that is connected to a microfluidic chip that can extract blood and/or interstitial fluid. The extracted fluid is then run over downstream transducers (i.e., electrode arrays, optical sensors, etc.) for either direct monitoring of physiological markers or monitoring after first being subject to post-processing reactions.

In one embodiment, microneedles are used as the puncturing tool. In vivo microneedles are known. They have been shown to be an effective and minimally invasive method for transdermal access for fluid exchange with living subjects. Microneedles are advantageous over conventional needles and lancets for some applications because they cause minimal discomfort. This is because microneedles do not interact with deeper layers of the dermis, which are associated with sensation and pain.

Thus, we have developed an in vivo microneedle platform integrated with multifunctional lab-on chip electrode arrays that can detect various diagnostic biomarkers. The microneedles are effective for extracting interstitial fluid that is directed through fluidic channels to electrochemical transducers for monitoring.

However, the needles can also be larger with dimensions in the millimeter-scale (e.g., 0.5 mm, 1 mm, 1.5 mm, 2 mm, 2.5 mm, 3 mm or more) to go deeper into a subject and extract blood as well as interstitial fluid. An anesthetic (such as, e.g., hirudin) can be secreted or used to coat the needle to minimize discomfort.

Accordingly, the present invention features a device for detecting one or more markers in a sample including: (i) a sensor component including at least one hollow needle and at least one sensing transducer in fluidic communication with at least one hollow needle, where at least one sensing transducer is configured to detect one or more markers in the sample; (ii) a delivery component including one or more depots containing one or more therapeutic agents; and (iii) an electronic component including circuitry configured for signal processing, signal control, power control, and/or communication signaling, where the electronic component is connected electrically to the sensor and delivery components.

In some embodiments, each needle has an interior surface facing the hollow lumen and an exterior surface, the distal end of the exterior surface for at least one needle includes a puncturing edge, and at least one needle has a length of more than about 0.5 mm or from about 0.1 mm to about 7 mm (e.g., from 0.1 mm to 0.5 mm, 0.1 mm to 1 mm, 0.1 mm to 1.5 mm, 0.1 mm to 2 mm, 0.1 mm to 2.5 mm, 0.1 mm to 3 mm, 0.1 mm to 3.5 mm, 0.1 mm to 4 mm, 0.1 mm to 4.5 mm, 0.1 mm to 5 mm, 0.2 mm to 0.5 mm, 0.2 mm to 1 mm, 0.2 mm to 1.5 mm, 0.2 mm to 2 mm, 0.2 mm to 2.5 mm, 0.2 mm to 3 mm, 0.2 mm to 3.5 mm, 0.2 mm to 4 mm, 0.2 mm to 4.5 mm, 0.2 mm to 5 mm, 0.2 mm to 7 mm, 0.3 mm to 0.5 mm, 0.3 mm to 1 mm, 0.3 mm to 1.5 mm, 0.3 mm to 2 mm, 0.3 mm to 2.5 mm, 0.3 mm to 3 mm, 0.3 mm to 3.5 mm, 0.3 mm to 4 mm, 0.3 mm to 4.5 mm, 0.3 mm to 5 mm, 0.3 mm to 7 mm, 0.5 mm to 1 mm, 0.5 mm to 1.5 mm, 0.5 mm to 2 mm, 0.5 mm to 2.5 mm, 0.5 mm to 3 mm, 0.5 mm to 3.5 mm, 0.5 mm to 4 mm, 0.5 mm to 4.5 mm, 0.5 mm to 5 mm, 0.5 mm to 7 mm, 0.7 mm to 1 mm, 0.7 mm to 1.5 mm, 0.7 mm to 2 mm, 0.7 mm to 2.5 mm, 0.7 mm to 3 mm, 0.7 mm to 3.5 mm, 0.7 mm to 4 mm, 0.7 mm to 4.5 mm, 0.7 mm to 5 mm, 0.7 mm to 7 mm, 1 mm to 1.5 mm, 1 mm to 2 mm, 1 mm to 2.5 mm, 1 mm to 3 mm, 1 mm to 3.5 mm, 1 mm to 4 mm, 1 mm to 4.5 mm, 1 mm to 5 mm, 1 mm to 7 mm, 1.5 mm to 2 mm, 1.5 mm to 2.5 mm, 1.5 mm to 3 mm, 1.5 mm to 3.5 mm, 1.5 mm to 4 mm, 1.5 mm to 4.5 mm, 1.5 mm to 5 mm, 1.5 mm to 7 mm, 3 mm to 3.5 mm, 3 mm to 4 mm, 3 mm to 4.5 mm, 3 mm to 5 mm, and 3 mm to 7 mm). In some embodiments, a plurality of microneedles is provided in an array (e.g., two, three, four, five, six, seven, eight, nine, ten, fifteen, twenty, or more needles in array).

In further embodiments, the (i) sensor component includes a substrate coupled to the plurality of hollow needles, where the substrate includes one or more inlets in fluidic communication with the proximal end of at least one needle; a first channel coupled to the substrate and in fluidic communication with at least one inlet of the substrate; and one or more sensing transducers (e.g., one or more electrodes, such as in an array) in fluidic communication with the first channel, where at least one sensing transducer is configured to detect one or more markers in the sample.

In other embodiments, the (ii) delivery component includes a plurality of hollow needles (e.g., any herein), where at least one needle is in fluidic communication with at least one depot containing or configured to contain one or more therapeutic agents. The depot can be any useful fluidic chamber, channel, or reservoir (e.g., any herein).

In some embodiments, the (iii) electronic component includes one or more components to operate the sensing transducer (e.g., a power source, a data-processing circuit powered by the power source and electrically connected to the transducer (e.g., a counter electrode, a reference electrode, and at least one said working electrode), and/or a data output port for the data-processing circuit). In other embodiments, components includes a battery, a pump fluidically connected to at least one hollow needle of the sensor component, and/or one or more electrical connections to one or more indicators (e.g., LED indicators).

In some embodiments, the device includes (iv) a fluidic component including one or more fluidic channels, chambers, pumps, and/or valves configured to provide fluidic communication between the sensor or delivery component and the sample.

In some embodiments, the device includes one or more mixing chambers, reaction chambers, reagents chambers, lysing chambers, washing chamber, elution chambers, extraction chambers, and/or collection chambers, where each of the chambers, if present, is in fluidic communication with the first channel. In other embodiments, the device includes at least one chamber in fluidic communication with another chamber (e.g., one or more reaction chambers in fluidic communication with at least one mixing chamber; one or more reagent chambers in fluidic communication with at least one mixing chamber and/or reaction chamber; one or more washing chambers in fluidic communication with at least one mixing chamber, reagent chamber, and/or reaction chamber).

In some embodiments, the plurality of hollow needles is configured to obtain the sample from a subject. In particular embodiments, at least one needle includes a puncturing edge (e.g., a tapered point, a sharpened bevel, or one or more prongs). In other embodiments, at least one hollow needle includes a polymer, a metal, silicon, glass, a composite material, or a combination thereof.

In some embodiments, the one or more sensing transducers is selected from an electrode (e.g., a planar electrode, a three-dimensional electrode, a porous electrode, a disk electrode, a spherical electrode, a plate electrode, a hemispherical electrode, a microelectrode, and a nanoelectrode, or an array thereof), an ion selective electrode (e.g., including a porous material and one or more ionophores), an optical sensor, an array of any of these, and combinations thereof. In particular embodiments, the sensing transducer includes an array of electrodes (e.g., optionally having a modified surface).

In some embodiments, the fluidic channel or fluidic component includes an array of channels configured for fluidic communication between one needle and an array of sensing transducers. In other embodiments, the array of channels is configured for fluidic communication between an array of needles and an array of sensing transducers. In another embodiment, the array of channels is configured for fluidic communication between an array of needles and an array of depots containing therapeutic agent(s).

In another aspect, the present invention features a device including an integral platform (e.g., a substrate), an array of one or more hollow-bored transdermal needles projecting from the platform, an array of one or more electrochemical working electrodes fixed within the platform and displaced from the needle array, and one or more fluidic channels defined within the platform, where each channel is coupled to the bore of at least one needle so as to duct sampled biological fluid therefrom, and where the one or more fluidic channels are conformed to direct sampled biological fluid from the needle array into contact with one or more electrochemical electrodes. One or more depots, e.g., associated with a needle array, can be included in order to deliver therapeutic agents to the user. This platform could be packaged in a modular form as well. For example, if the fluidics encompasses sample processing, the needle array, depots, and electrode array may be modular for easy disposal whereas the microfluidic sample processing is reusable.

In one embodiment, each fluidic channel is arranged to direct the sample (e.g., sampled biological fluid) from a respective needle to one or more electrodes that are particular to the respective needle.

In some embodiments, the working electrodes include gold, indium tin oxide, and/or carbon. In yet other embodiments, the working electrodes are chemically surface-modified to facilitate the bioassay. In various embodiments, the working electrodes are chemically surface-modified to facilitate immunoassay to detect one or more protein markers (e.g., troponin and/or myoglobin).

In one embodiment, the device further includes an electrochemical reference electrode and an electrochemical counter electrode fixed within the platform.

In another embodiment, the device further includes at least one mixing chamber defined within the platform, at least one reservoir defined within the platform, and at least one controllable valve for releasing a reagent or diluent from a reservoir into a mixing chamber.

In one embodiment, the platform further includes a pump configured to facilitate the flow of the sample (e.g., sampled biological fluid) from at least one needle toward at least one working electrode. In another embodiment, the platform includes a pump configured to facilitate delivery of one or more therapeutic agents from at least one needle to a target site of the subject or user. In yet another embodiment, the platform includes a pump configured to return analyzed fluid (i.e., after testing or detecting with a transducer or sensor component) from at least one needle toward the target site of the subject or user.

In one embodiment, the device further includes a power source and a data-processing circuit powered by the power source and electrically connected to a counter electrode, a reference electrode, and at least one said working electrode. In some embodiments, the device further includes a data output port for the data-processing circuit.

In one embodiment, the device further includes a telemetry unit configured to receive processed data from the data-processing circuit and to transmit the data wirelessly. In various embodiments, the telemetry unit is fixed within the platform or packaged separately from the platform and connected thereto by a cable.

In another aspect, the present invention features a kit including a device of the invention (e.g., any described herein) and instructions for affixing the device to a subject and activating the device. In further embodiments, the kit includes a therapeutic agent selected from the group consisting of an anesthetic, an antiseptic, an anticoagulant, a drug, and a vaccine. In yet other embodiments, the kit includes a telemetry unit optionally including a cable.

The present invention also features methods of detecting and/or monitoring one or more markers in a sample (e.g., blood, plasma, serum, transdermal fluid, interstitial fluid, sweat, or a bodily fluid, as well as any sample herein). In some embodiments, the method includes obtaining the sample from a subject using the device of the invention (e.g., optionally including affixing the device to the subject) and activating the device, thereby detecting one or more markers in the sample. In further embodiments, the method includes remotely relaying the results of the presence or absence of one or more markers. In yet other embodiments, the method includes delivering one or more therapeutic agents (e.g., any herein) to the subject.

In any of the embodiments herein, at least one needle, substrate (e.g., PCB), fluidic channel, chamber, depot, and/or sensing transducer further includes a modified surface (e.g., surface-modified with one or more capture agents, such as one or more antibodies for detecting one or more markers, enzymes, etc., as well as any described herein). In other embodiments, the modified surface includes a conductive material (e.g., a conductive polymer, such as poly(bithiophene), polyaniline, or poly(pyrrole), such as dodecylbenzenesulfonate-doped polypyrrole; a metal, such as metal nanoparticles, metal microparticles, or a metal film; or a nanotube). In yet other embodiments, the modified surface includes a linking agent (e.g., a diazonium compound, as described herein). In further embodiments, the modified surface includes a label (e.g., optionally attached to a surface by a linking agent).

In any of the embodiments herein, at least one needle (e.g., disposed within the lumen, on the interior surface, and/or on the exterior surface), substrate, fluidic channel (e.g., disposed within the channel), chamber, depot, and/or sensing transducer (e.g., disposed on one or more electrodes, dielectrics, etc.) further includes a substance (e.g., one or more capture agents, electroactive components, linking agents, or any substance described herein).

In any of the embodiments herein, the needles, first channel, fluidic components, fluidic channels, chambers, depots, and/or transducers are, independently, provided in a high-density array. In further embodiments, the high-density array includes a modified surface (e.g., further including a linking agent, such as any described herein, including a diazonium compound).

In any of the embodiments herein, the device includes one or more components (e.g., the plurality of hollow needles, the substrate, the first channel, and the one or more transducers, as well as the sensor, delivery, electrical, and fluidic components) integrated into a single structure (e.g., a monolithic structure, where each of the components are bonded together to form a single structure). In further embodiments, each of the components (e.g., the plurality of hollow needles, the substrate including the needles, the first channel, and the one or more transducers, as well as the sensor, delivery, electrical, and fluidic components) is embedded in the same substrate. In further embodiments, each of the components (e.g., the plurality of hollow needles, the substrate including the needles, the first channel, and the one or more transducers, as well as the sensor, delivery, electrical, and fluidic components) is embedded in different substrates (e.g., where the different substrates are bonded to form a multilayer device).

In any of the embodiments herein, the device includes one or more components (e.g., the plurality of hollow needles, the substrate, the first channel, and the one or more transducers, as well as the sensor, delivery, electrical, and fluidic components) configured into separate modules (e.g., reusable, refillable, and/or disposable modules).

In any of the embodiments herein, the device includes multiples substrates (e.g., configured in multiple layers).

In any of the embodiments herein, the device is configured in a package (e.g., a packaged chip having a housing for the device of the invention).

In any of the embodiments herein, the device further includes one or more components for relaying the presence or absence of one or more markers in the sample. Exemplary components include a data output port for the data-processing circuit, an analog-to-digital converter, a radiofrequency module, a cable, and/or a telemetry unit (e.g., configured to receive processed data from a data-processing circuit electrically connected to the transducer and to transmit the data wirelessly).

In any of the embodiments herein, the device includes one or more of a filter, a permeable or semi-permeable membrane, a valve, a chamber (e.g., any described herein, including reservoirs), a pump, a probe, a multifunctional sensor, a feedback resistor, a microscale light-emitting diode, an active/passive circuit element, an actuator, a wireless power coil, a device for radio frequency (RF) communications, a temperature sensor, a photodetector, a photovoltaic cell, a diode, and/or a liner with an adhesive layer (e.g., for affixing the device to a user).

Definitions

By "about" is meant+/−10% of any recited value.

By "fluidic communication," as used herein, refers to any duct, channel, tube, pipe, reservoir, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

As used herein, "linked" or "linking" is understood to mean attached or bound by covalent bonds, non-covalent bonds, and/or linked via van der Waals forces, hydrogen bonds, and/or other intermolecular forces.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm. In another instance, a microneedle can have a length, width, height, cross-sectional dimension, circumference, radius (e.g., external or internal radius), or diameter that is less than 1 mm.

By "treating" a disease, disorder, or condition in a subject is meant reducing at least one symptom of the disease, disorder, or condition by administrating a therapeutic substance to the subject.

By "treating prophylactically" a disease, disorder, or condition in a subject is meant reducing the frequency of occurrence or severity of (e.g., preventing) a disease, disorder or condition by administering to the subject a therapeutic substance to the subject prior to the appearance of a disease symptom or symptoms.

By "sample" is meant any specimen obtained from a subject, a plant, an environment, a chemical material, a biological material, or a manufactured product. The sample can include any useful material, such as biological (e.g., genomic) and/or chemical matter.

By "subject" is meant a human or non-human animal (e.g., a mammal). Exemplary non-human animals include livestock (e.g., cattle, goat, sheep, pig, poultry, farm fish, etc.), domestic animals (e.g., dog, cat, etc.), or captive wild animals (e.g., a zoo animal).

DETAILED DESCRIPTION OF THE INVENTION

Figure 1A:
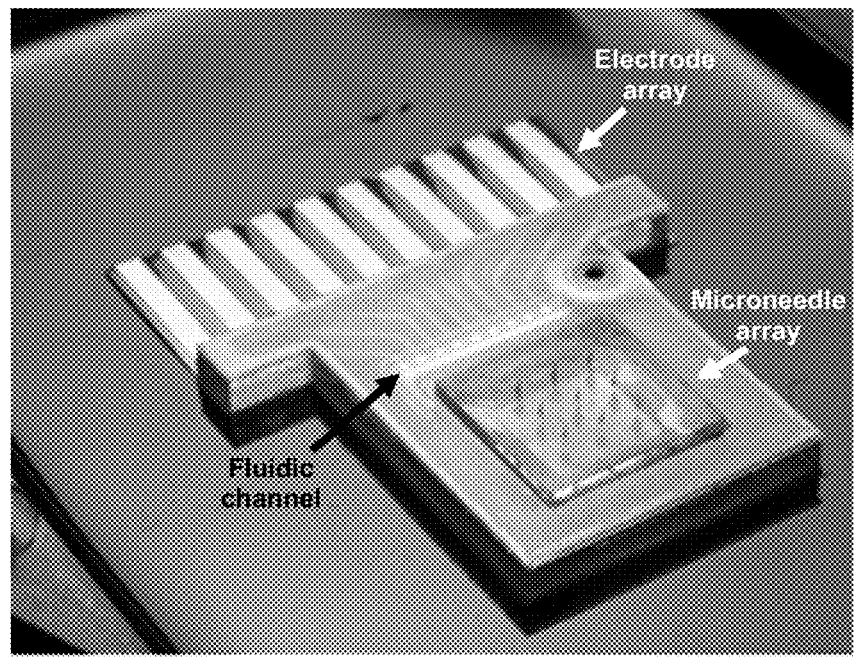
FIG. 1A-1B provides (A) a perspective view of an exemplary device according to an embodiment of the invention and (B) a photograph of an exemplary microneedle.

We developed a hollow microneedle manifold integrated on the same platform with an electrode array and a fluidic channel. In one example, we fabricated an eight-channel electrode array using photolithographic patterning and dielectric insulating layers to expose a 112 µm wide by 150 µm gold working area. The resulting chip was packaged using plastic laminate technology with a fluidic channel that could access the microneedles and flow solution over the electrode array. This type of device is a significant advancement towards an autonomous microneedle platform, which is capable of transdermally accessing interstitial fluid and performing real time and repeated measurements for a variety of physiologically relevant analytes. A non-limiting example of our device is illustrated in FIG. 1.

More specifically, a microfluidic manifold was constructed from acrylic sheets and medical grade pressure sensitive adhesive (PSA, e.g., Mylar® adhesives, which is a polyethylene terephthalate film) using a precision cutting laser. The acrylic sheets were typically 2 mm in thickness, although thinner or thicker sheets could be used depending on the particular application contemplated, the mechanical robustness associated with the intended function, and the form factor. Medical grade PSA was chosen because it is frequently used in the construction of commercial bioassay devices; it has demonstrated low outgassing, low chemical leaching, and biocompatibility.

Each of the materials used for construction was cut with a laser and sequentially assembled on a jig to create complex fluidic networks, with lateral flow channels being formed in the adhesive layers and connecting vias being formed in the acrylic sheet. After the layers were stacked and assembled, they were pressed together for 2 minutes at 500 psi to assure adhesion of the laminate layers. Our example design has one acrylic layer and two adhesive layers. The bottom adhesive layer forms the flow channel on the surface of the electrochemistry sensing chip, and the top adhesive layer seals the microneedles to the laminate cartridge. Based on the desired functionality, a skilled artisan would be able to include additional layers and structures to control flow of the sample, reagents, etc.

For external fluid connections, we enclosed conventional Viton rubber O-rings (size 001) within the cartridge. Inserting $\frac{1}{32}$" tubing into these captured O-rings can create a fluid-tight seal so that the application of positive or negative pressure can cause fluid to be injected or drawn through the microneedle array.

Hollow microneedles can be prepared using a laser direct write system utilizing two-photon polymerization (2PP). First, a CAD file was created in the desired shape and dimensions of the microneedle and was uploaded to the LDW operating software (GOLD3D). The software sliced the CAD file and assigned laser and writing parameters such that the fabrication process can be optimized.

The two-photon polymerization effect is achieved with the help of Ti:Sapphire laser, which was operated at 800 nm, 150 fs, and 76 MHz. Eshell 300 was used as the resin for both the hollow microneedles and the substrates. The substrate can be formed by any useful process, e.g., such as any described herein. The process can include, without limitation, stereolithography, 2PP, etc., including any combinations thereof.

A first substrate can be used as a "base" to fabricate the needle, lancet, or puncturing mechanism onto and to be later integrated into a second substrate for the microfluidic chip. The first substrate is made so that it either fits within a recess on the microfluidic chip or acts as the top layer of the microfluidic chip. Furthermore, the transducer can be formed in a third substrate, which is integrated with the chip having one or more fluidic channels. Alternatively, the needles, microfluidic chip, and transducers are formed in the same substrate.

Substrates are made either with the 2PP system, a stereolithography system, by molding, by casting, or any other useful method. In particular, the 2PP system allows us to selectively polymerize a resin based on a CAD file to create the microneedles, and we choose a substrate made from the same material or similar material so that the chemical bonds between the microneedle and substrate are the same, which creates a strong bond between the two.

Figure 2:
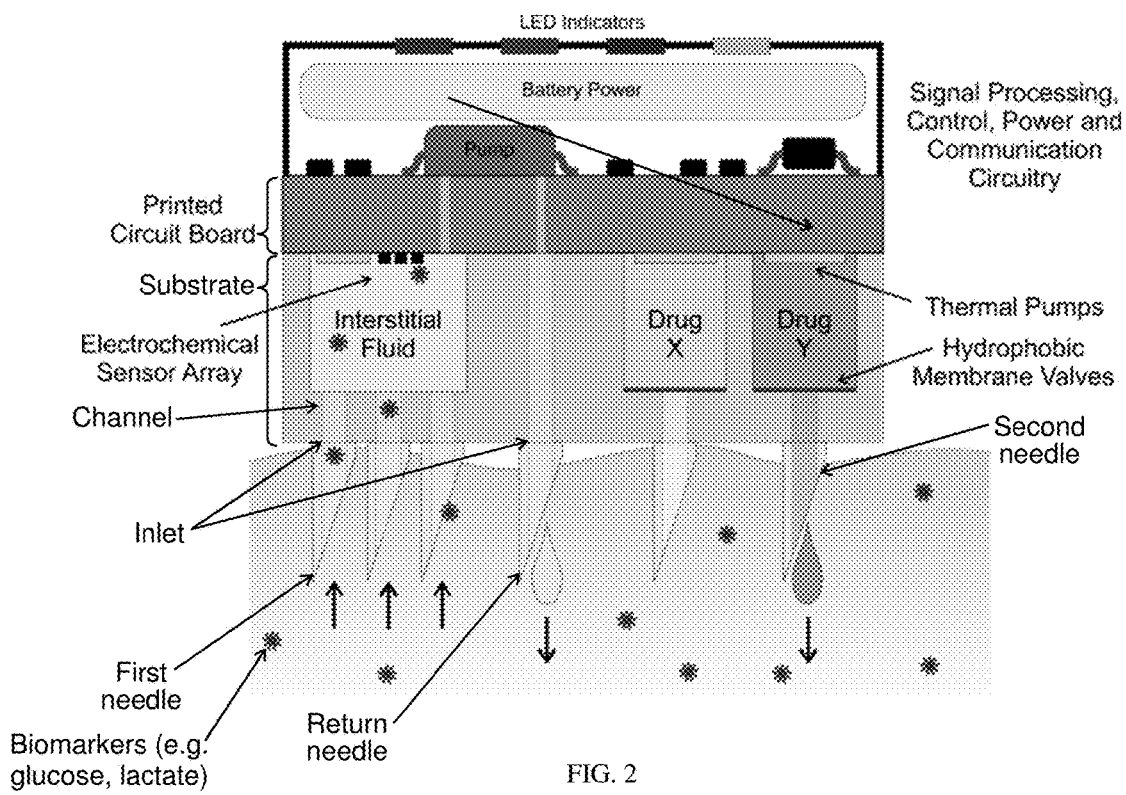
FIG. 2 provides a schematic of an exemplary device including a microneedle manifold, fluidic connections, drug chambers or depots, a printed circuit board (PCB), and electronic components (e.g., a pump, battery, and LED indicators).

The substrates were created in PDMS molds made by laser cutting PMMA to 10 mm×10 mm×2 mm pieces and molding them with PDMS. Eshell 300 was then placed in the molds and cured with a UV lamp. In order to make a fluidic connection between the microfluidic chip and the hollow microneedle, a bore was cut into the substrates with a $CO_2$ laser such that the bore diameter was around 150 µm. A well was made on top of the bore-containing substrate such that a microneedle could be written onto the substrate. FIG. 2 provides an example of a fabricated microneedle.

FIG. 1 provides, among other things, a view of an exemplary electrode array including eight working electrodes, a counter electrode, and a reference electrode. The eight working elements were integrated with the microneedle array.

Six-inch-diameter glass wafers were used as substrates for the electrode arrays. Standard photolithography techniques were used to pattern 150 Å Cr/3000 Å Au electrodes and contact pads. In order to precisely define the electrode surface area, a 2000 Å thick silicon nitride layer was deposited at 350° C. over the entire device using PECVD. A photolithography step defined a precise opening over the dielectric layer, which measured 112 µm wide by 150 µm high. An $SF_6$ plasma etch was then used to selectively remove the exposed silicon nitride until the Au layer underneath was reached.

The electrode array can be optimized for immunoassays to detect troponin, myoglobin, or any other useful biomarker (e.g., any described herein). For instance, troponin and myoglobin are used in the clinical setting as biomarkers for detection of cardiac and skeletal muscle injuries, respectively. This approach can include a sandwich antibody assay, consisting of a capture antibody and a secondary detection antibody labeled with a horseradish peroxidase enzyme that catalyzes conversion of a 3,3',5,5'-tetramethylbenzidine (TMB) substrate to an electrochemically-detectable product.

Needles

The device of the invention can have one or more needles of any useful dimension, such as length, width, height, circumference, and/or cross-sectional dimension. In particular, a skilled artisan would be able to optimize the needle length based on the type of fluid or type of tissue to be measured. For instance, the skin can be approximated as two layers including the epidermis (thickness of 0.05 to 1.5 mm) and the dermis (thickness of 0.3 to 3 mm). Accordingly, to obtain fluid in the dermis layer, the needle can be optimized to have a length that is more than about 0.3 mm, 0.5 mm, 1 mm, 1.5 mm, 2 mm, 2.5 mm, or 3 mm, depending on the desired location of the device on the body. A desired cross-sectional dimension can be determined by the skin site to be sampled (e.g., a dimension to allow for local testing of the subject, while minimizing pain), by the desired flow rate of the sample within the lumen of the needle (e.g., the flow rate can be optimized to allow for obtaining a fluid within a particular sampling time, or to minimize sample contamination, coagulation, and/or discomfort to the subject), by the desired volume of sample to be collected, etc.

To access a sample within a subject, each needle can have one or more puncturing edges of any useful geometry. In some embodiments, the puncturing edge at the distal end of the needle includes a tapered point. In particular embodiments, the tapered point is located at the apex of a pyramidal needle, where the base of the needle is attached to the substrate and one side of the pyramidal needle is open, thereby forming the lumen of the needle. An exemplary pyramidal needle is provided in FIG. 2 herein. In yet other embodiments, the puncturing edge is a sharpened bevel for any useful geometrical shape forming the hollow needle, such as a cylinder, a cone, a post, a rectangle, a square, a trapezoid, as well as tapered forms thereof (e.g., a tapered cylinder or a tapered post), etc. In further embodiments, the puncturing edge includes one or more prongs (e.g., two, three, four, five, or more prongs) for obtaining a sample from a subject.

In some embodiments, the device includes a return needle configured to return tested or analyzed fluid back to the target site. For instance, as shown in FIG. 2 (third needle from the right), a needle can be used to re-inject interstitial fluid back into the subject. In this way, additional storage chambers will not be needed on-chip to store tested samples. Alternatively, the device can include one or more compartments to maintain tested samples for further or later testing.

The needles can be formed from any useful material, e.g., a polymer (e.g., such as a biocompatible polymer; an acrylate-based polymer, such as e-Shell 200 (0.5-1.5% wt phenylbis(2,4,6 trimethylbenzoyl)-phosphine oxide photoinitiator, 15-30% wt propylated (2) neopentyl glycoldiacrylate, and 60-80% wt urethane dimethacrylate) or e-Shell 300 (10-25% wt urethane dimethacrylate and 10-20% tetrahydrofurfuryl-2-methacrylate); a resorbable polymer, e.g., polyglycolic acid (PGA), polylactic acid (PLA) including poly(L-lactide) (PLLA) and poly(D-lactide) (PDLA), or PGA-PLA copolymers; or any described herein), silicon, glass, a metal (e.g., stainless steel, titanium, aluminum, or nickel, as well as alloys thereof), a composite material, etc. The surface (e.g., interior and/or exterior surface) of the needle can be surface-modified with any agent described herein (e.g., a linking agent, capture agent, label, and/or porous material, as described herein). Additional surface-modified needles are described in U.S. Pub. No. 2011/0224515, as well as U.S. Pat. Nos. 7,344,499 and 6,908,453, each of which is incorporated by reference herein in its entirety.

The needles can be formed from any useful process. For instance, when formed from a polymer, the needle can be formed by two-photon polymerization (2PP), as described, e.g., in Gittard S D et al., "Fabrication of polymer microneedles using a two-photon polymerization and micromolding process," *J. Diabetes Sci. Technol.* 2009; 3:304-11, which is incorporated by reference in its entirety. Additional methods include polymerizing, molding (e.g., melt-molding), spinning, depositing, casting (e.g., melt-casting), etc. Methods of making needles are described in U.S. Pat. Nos. 7,344,499 and 6,908,453, each of which is incorporated by reference herein in its entirety.

Furthermore, a plurality of needles can be provided in an array. The array can include two, three, four, five, six, seven, eight, nine, ten, fifteen, twenty, or more needles configured in any useful arrangement (e.g., geometrical arrangements). The array can have any useful spatial distribution of needles (e.g., a square, rectangular, circular, or triangular array), a random distribution, or the like.

The needle can include any useful substance, e.g., any described herein. In particular embodiments, one or more needles includes a substance that further includes one or more capture agents. For example, the needle can include (e.g., within a portion of the lumen of the needle) a matrix including an electroactive component. The electroactive component can be, e.g., a carbon paste including one or more capture agents (e.g., an enzyme or a catalyst (e.g., rhodium) for detecting a marker). Further embodiments are described in Windmiller J R et al., "Microneedle array-based carbon paste amperometric sensors and biosensors," *Analyst* 2011; 136:1846-51, which is incorporated by reference in its entirety.

Exemplary needles are described in U.S. Pub. No. 2011/0224515; and Int. Pub. No. WO 2013/058879, each of which is incorporated by reference in its entirety.

Transducers

The transducer can be any useful structure for detecting, sensing, and/or measuring a marker or target of interest. Exemplary transducers include one or more of the following: optical sensors (e.g., including measuring one or more of fluorescence spectroscopy, interferometry, reflectance, chemiluminescence, light scattering, surface plasmon resonance, or refractive index), piezoelectric sensors (e.g., including one or more quartz crystals or quartz crystal microbalance), electrochemical sensors (e.g., one or more of carbon nanotubes, electrodes, field-effect transistors, etc.), etc., as well as any selected from the group consisting of an ion selective electrode, an ion sensitive field effect transistor (e.g., a n-p-n type sensor), a light addressable potentiometric sensor, an amperometric sensor (e.g., having a two-electrode configuration (including reference and working electrodes) or a three-electrode configuration (including reference, working, and auxiliary electrodes)), and/or an impedimetric sensor.

In particular embodiments, the transducer is a working electrode having an exposed working area. The working electrode includes any useful conductive material (e.g., gold, indium tin oxide, titanium, and/or carbon). Optionally, the working area is surface modified, e.g., with a linking agent and/or a capture agent described herein. These transducers can include one or more other components that allows for detection, such as a ground electrode, a reference electrode, a counter electrode, a potentiostat, etc. The electrode can have any useful configuration, such as, e.g., a disk electrode, a spherical electrode, a plate electrode, a hemispherical electrode, a microelectrode, or a nanoelectrode; and can be formed from any useful material, such as gold, indium tin oxide, carbon, titanium, platinum, etc.

Exemplary electrodes include a planar electrode, a three-dimensional electrode, a porous electrode, a post electrode, a microelectrode (e.g., having a critical dimension on the range of 1 to 1000 µm, such as a radium, width, or length from about 1 to 1000 µm), a nanoelectrode (e.g., having a critical dimension on the range of 1 to 100 nm, such as a radium, width, or length from about 1 to 100 nm), as well as arrays thereof. For instance, a three-dimensional (3D) electrode can be a three-dimensional structure having dimensions defined by interferometric lithography and/or photolithography. Such 3D electrodes can include a porous carbon substrate. Exemplary 3D porous electrodes and methods for making such electrodes are described in U.S. Pat. No. 8,349,547, which is incorporated herein by reference in its entirety. In another embodiment, the electrode is a porous electrode having a controlled pore size (e.g., a pore size less than about 1 µm or about 0.1 µm). In some embodiments, the electrode is a post electrode that is a carbon electrode (e.g., formed from a photoresist (e.g., an epoxy-based resist, such as SU-8) that has been pyrolyzed), which can be optionally modified by depositing a conductive material (e.g., a conductive polymer or a metal, such as any described herein). In yet other embodiments, the electrode is a nanoelectrode including a nanodisc, a nanoneedle, a nanoband, a nano-electrode ensemble, a nanoelectrode array, a nanotube (e.g., a carbon nanotube), a nanopore, as well as arrays thereof. Exemplary nanoelectrodes are described in Arrigan D W M, "Nanoelectrodes, nanoelectrode arrays and their applications," *Analyst* 2004 December; 129(12):1157-65, which is incorporated by reference herein in its entirety.

Any of these electrodes can be further functionalized with a conductive material, such as a conductive polymer, such as any described herein, including poly(bithiophene), polyaniline, or poly(pyrrole), such as dodecylbenzenesulfonate-doped polypyrrole; a metal, such as metal nanoparticles (e.g., gold, silver, platinum, and/or palladium nanoparticles), metal microparticles, a metal film (e.g., palladium or platinum), etc.; a nanotube; etc. Additional electrodes are described in Int. Pub. No. WO 2013/058879 and U.S. Pat. No. 8,349,547, each of which is incorporated herein by reference in its entirety.

The needles and transducers can be configured in any useful manner. For instance, the needles and transducers can be fluidically connected by a fluidic channel. In other embodiments, the needle can include a transducer within the lumen of a needle, such as those described in Int. Pub. No. WO 2013/058879, which is incorporated by reference in its entirety. In some embodiments, the needle can include a transducer on the exterior surface of the needle. For instance, the transducer can include one or more conductive layers on the exterior surface of the needle, where the conductive layer can include one or more capture agents (e.g., any described herein). Such needles and conductive layers, as well as sensing layers and protective layers, are described in, e.g., Int. Pub. No. WO 2006/116242, which is incorporated herein by reference in its entirety.

The transducer can be integrated with the needle by any useful process and with any useful configuration. For example, the transducer can be a carbon fiber electrode configured to reside within the lumen of a needle. Such a configuration is described, e.g., in Miller P R et al., "Integrated carbon fiber electrodes within hollow polymer microneedles for transdermal electrochemical sensing," *Biomicrofluidics* 2011; 5:013415 (14 pages), which is incorporated herein by reference in its entirety.

The present invention could also allow for integration between one or more needles with an array of transducers. The needle and electrode can be configured in any useful way. For instance, each needle can be associated with a particular electrode, such that there is a one-to-one correspondence between the fluid withdrawn into the needle and the fluid being delivered to the electrode. In other embodiments, each needle is associated with an array of electrodes. In yet other embodiments, an array of needles is associated with an individual electrode or with an array of electrodes.

The fluidic connection between the needle and the electrode can be established by a channel or a network of channels. In one non-limiting example, when one needle is associated with an array N×M of electrodes, a network containing channels can be interfaced between the needle and electrode array. Such a network can include a main channel that splits into N sub-channels, which in turn split into M smaller channels. A skilled artisan would understand how to optimize channel geometry to fluidically connect one or more needles to one or more electrodes.

In some embodiments, the array is a high density array including N×M array of electrodes, where each electrode can be individually addressable. In further embodiments, the high density array is surface modified with one or more capture agents and/or one or more linking agents, as described herein. Exemplary values for N and M include, independently, 1, 2, 3, 4, 5, 6, 7, 8, 9, 10, 12, 15, 20, 25, 30, 40, 50, 75, 100, etc.

The transducers can optionally be surface-modified with one or more capture agents (e.g., one or more antibodies for detecting one or more markers, such as any described herein). Such transducer can include, e.g., an ion selective electrode (ISE) for detecting one or more ions. An ISE can include a porous material and one or more capture agents, such as, e.g., one or more ionophores. Exemplary porous materials include porous carbon, graphene, silicon, conducting polymer (e.g., such as any described herein), etc. Exemplary ionophores include one or more of the following: a crown ether, a macrocyclic compound, a cryptand, a calixarene, A23187 (for $Ca^{2+}$), beauvericin (for $Ca^{2+}$, $Ba^{2+}$), calcimycine (for A23187), enniatin (for ammonium), gramicidin A (for $H^+$, $Na^+$, $K^+$), ionomycin (for $Ca^{2+}$), lasalocid, monensin (for $Na^+$, $H-$), nigericin (for $K^+$, $H^+$, $Pb^{2+}$), nonactin (for ammonium), nystatin, salinomycin (for $K^+$), valinomycin (for $K^+$), siderophore (for $Fe^{3+}$), etc. Such materials and ISEs can be obtained by any useful process, such as templating (see, e.g., Lai C et al., *Anal. Chem.* 2007; 79:4621-6), interference lithography, molding, casting, spinning, electrospinning, and/or depositing.

Another exemplary transducer includes a detection electrode configured for a sandwich assay. Such an electrode include, e.g., a conductive surface and a first capture agent (e.g., an antibody) immobilized on the conductive surface, where the first capture agent is optionally attached by a linking agent. In use, the marker of interest binds to the first capture agent to form a complex, and further capture agents can be used to bind the resultant complex. To detect the complex, further capture agents can include a detectable label or an enzyme that reacts with an agent to provide a detectable signal (e.g., an agent that is a fluorogenic, enzyme-cleavable molecule).

Substrate

In general, a substrate refers to a substantially planar surface or media containing one or more structures. For instance, one or more needles, fluidic channels, transducers, fluidic component, sensor component, delivery component, and/or electronic component can be embedded in the same substrate or in different substrates. The substrate can be formed from any useful material. Exemplary materials include any described herein, such as a flexible substrate (e.g., a polyvinylacetate, a polyester, or any other described herein) or a printed circuit board (PCB).

The substrate can include one or more inlets in fluidic communication with the needle. In this manner, a sample collected within the needle can be delivered through the needle and into the inlet. Generally, the inlet is further configured to be in fluidic communication with one or more fluidic channels, as described herein. Such fluidic channels allow the sample to be delivered to one or more sensing transducers, thereby detecting the marker of interest.

When the substrate is the PCB, then one or more vias can be present for fluidic communication between the needle and a pump (e.g., by way of a fluidic component or channel). In this way, pumps can be used to withdraw additional sample (e.g., a sample of interstitial fluid) into the needle manifold for monitoring and detecting one or more markers.

Other structures can be integrated into a substrate, such as, e.g., a filter, a permeable or semi-permeable membrane, a valve, and/or an electrode (e.g., any described herein).

Furthermore, the device of the invention can include multiple substrates (e.g., configured in multiple layers). For ease of manufacturing, the needles can be manufactured in a first substrate, other structures (e.g., fluidic channels and/or depots) can be included in a second substrate, and the transducer(s) can be included in a third substrate. An electronic component can be included as a fourth substrate (e.g., as a PCB substrate). Alternatively, the transducer(s) can be deposited on the PCB substrate. Then, the first, second, third, and fourth substrates, if present, are aligned (e.g., by including one or more registration marks or alignment holes on each substrate) and then laminated (e.g., by using an adhesive layer between substrate layers). A skilled artisan would be able to optimize manufacturing parameters for the particular design of the device and arrangement of these various structures.

Fluidic Channels, Chambers, and Depots

One or more fluidic channels (including inlets), chambers, and depots can be used to effect fluidic communication between two structures or regions. In particular embodiments, depots are fluidic chambers configured to store one or more therapeutic agents.

The present invention could also allow for integration between one or more needles with an array of depots. For instance, each needle can be associated with a particular depot, such that there is a one-to-one correspondence between the type of therapeutic agent being injected into the user and one particular needle. In other embodiments, each needle is associated with an array of depots. In yet other embodiments, an array of needles is associated with an individual depot or with an array of depots. The fluidic connection between the needle and the depots can be established by a channel or a network of channels.

Any of the fluidic channels, chamber, and depots described herein can be surface modified (e.g., to increase biocompatibility, decrease protein adsorption or absorption, and/or decrease surface contamination). Furthermore, such fluidic channels, chamber, and depots can also include one or more capture agents to selectively or non-selectively bind to cellular components or contaminants within a sample.

Surface Modification

Any of the surfaces described herein may be modified to promote biocompatibility, to functionalize a surface (e.g., using one or more capture agents including the optional use of any linking agent), or both. Exemplary surfaces include those for one or more transducers, needles, fluidic channels, depots, filters, and/or substrates (e.g., a PCB substrate).

The surface can be modified with any useful agent, such as any described herein. Exemplary agents include a capture agent (e.g., any described herein, such as an antibody); a polymer, such as a conducting polymer (e.g., poly(pyrrole), poly(aniline), poly(3-octylthiophene), or poly(thiophene)), an antifouling polymer, or a biocompatible polymer (e.g., chitosan), or a cationic polymer)); a coating, e.g., a copolymer, such as a copolymer of an acrylate and a lipid, such as butyl methacrylate and 2-methacryloyloxyethyl phosphorylcholine; a film; a label (e.g., any described herein); a linking agent (e.g., any described herein); an electroactive component, such as one or more carbon nanotubes or nanoparticles (e.g., gold, copper, cupric oxide, silver, or platinum nanoparticles), such as, for stabilizing an electrode; an enzyme, such as glucose oxidase, cholesterol oxidase, horse radish peroxidase, or any enzyme useful for oxidizing, reducing, and/or reacting with a marker of interest; or combinations thereof (e.g., an electroactive component coated with a polymer, such as a carbon nanotube coated with polyaniline).

Optionally, linking agents can be used be attach the agent to the surface. Exemplary linking agents include compounds including one or more first functional groups, a linker, and one or more second functional groups. In some embodiments, the first functional group allows for linking between a surface and the linker, and the second functional group allows for linking between the linker and the agent (e.g., a capture agent, a label, or any agent described herein). Exemplary linkers include any useful linker, such as polyethylene glycol, an alkane, and/or a carbocyclic ring (e.g., an aromatic ring, such as a phenyl group). In particular embodiments, the linking agent is a diazonium compound, where the first functional group is a diazo group ($-N_2$), the linker is an aryl group (e.g., a mono-, bicyclic, or multicyclic carbocyclic ring system having one or two aromatic rings and is exemplified by phenyl, naphthyl, xylyl, 1,2-dihydronaphthyl, 1,2,3,4-tetrahydronaphthyl, fluorenyl, indanyl, indenyl, and the like), and the second functional group is a reactive group for attaching a capture agent or a label (e.g., where the second functional group is halo, carboxyl, amino, sulfo, etc.). Such diazonium compounds can be used to graft an agent onto a surface (e.g., an electrode having a silicon, iron, cobalt, nickel, platinum, palladium, zinc, copper, or gold surface). In some embodiments, the linking agent is a 4-carboxybenzenediazonium salt, which is reacted with a capture agent by 1-ethyl-3-[3-dimethylaminopropyl]carbodiimide hydrochloride (EDC)/N-hydroxysuccinimide (NHS) crosslinking, to produce a diazonium-capture agent complex. Then, this resultant complex is deposited or grafted onto a surface (e.g., an electrode surface).

Other exemplary linking agents include pairs of linking agents that allow for binding between two different components. For instance, biotin and streptavidin react with each other to form a non-covalent bond, and this pair can be used to bind particular components. As shown in FIG. 9, e.g., a first capture agent is an antibody attached to a substrate with a diazonium linking agent, a second capture agent is an antibody labeled with biotin (labeled "B"), and a third capture agent is an enzyme labeled with streptavidin (labeled "A").

Additional Components

The present device can include any useful additional component. Exemplary components include those provided for a transducer (e.g., any described herein, as well as those in Justino C I L et al., "Review of analytical figures of merit of sensors and biosensors in clinical applications," *Trends Analyt. Chem.* 2010; 29:1172-83, which is incorporated by reference in its entirety); those provided for a microneedle (e.g., any described herein, as well as those in Gittard S D et al., "Two photon polymerization of microneedles for transdermal drug delivery," *Exp. Opin. Drug Deliv.* 2010; 7(4):513-33, and Miller P R et al., "Multiplexed microneedle-based biosensor array for characterization of metabolic acidosis," *Talanta* 2012; 88:739-42, each of which is incorporated by reference in its entirety); a membrane (e.g., placed between the needle and the channel; placed within a channel, such as to filter one or more particles within the sample; and/or placed between the channel and the electrode); a multifunctional sensor (e.g., to measure temperature, strain, and electrophysiological signals, such as by using amplified sensor electrodes that incorporate silicon metal oxide semiconductor field effect transistors (MOSFETs), a feedback resistor, and a sensor electrode in any useful design, such as a filamentary serpentine design); a microscale light-emitting diode (LEDs, such as for optical characterization of the test sample); an active/passive circuit element (e.g., such as transistors, diodes, and resistors); an actuator; a wireless power coil; a device for radio frequency (RF) communications (e.g., such as high-frequency inductors, capacitors, oscillators, and antennae); a resistance-based temperature sensor; a photodetector; a photovoltaic cell; and a diode, such as any described in Kim N et al., *Science* 2011; 333:838-43, which is incorporated herein by reference. These components can be made from any useful material, such as, e.g., silicon and gallium arsenide, in the form of filamentary serpentine nanoribbons, micromembranes, and/or nanomembranes.

The present device can include one or more structural components within the integral platform or substrate. Exemplary components include a mixing chamber in fluidic communication with the lumen of a needle; a reservoir optionally including one or more reagents (e.g., any described herein), where the reservoir can be in fluidic communication with the mixing chamber or any fluidic channel; a cell lysis chamber (e.g., configured to lyse one or more cells in a sample and in fluidic communication with needle and the sensing transducer); a controllable valve (e.g., configured to release a reagent from a reservoir into a mixing chamber); a pump (e.g., configured to facilitate flow of a sample to the transducer and/or through one or more fluidic channels); a waste chamber (e.g., configured to store a sample after detection of one or more reagents); a probe; and/or a filter (e.g., configured to separate one or more components from the sample either before or after detection with the transducer).

In some embodiments, the needle can be configured to be in fluidic communication with a reservoir (e.g., containing a drug for delivery and/or a reagent for detecting the marker of interest). Such a configuration can optionally include a valve between the needle and reservoir. In other embodiments, a probe can be configured to be in fluidic communication with the lumen of the needle. Exemplary needles and probes are described in Int. Pub. No. WO 2013/058879 (e.g., in FIG. 1A-1D, FIG. 1L, FIG. 2A-2C, FIG. 5A-5D, FIG. 12A-12B, FIG. 17, FIG. 18A-18D, and its related text), which is incorporated herein in its entirety.

The device can include one or more components to operate a transducer. For instance, in some embodiments, the transducer is an electrode or an array of electrodes. Accordingly, the device can further include a power source to operate the electrode. In particular embodiments, the device includes a data-processing circuit powered by the power source and electrically connected to the transducer (e.g., a counter electrode, a reference electrode, and at least one said working electrode). In further embodiments, the device includes a data output port for the data-processing circuit. Such data from the transducer can include any useful information, such as electromotive force (EMF), potentiometric, amperometric, impedance, and/or voltammetric measurements. Other data can include fluorometric, colorimetric, optical, acoustic, resonance, and/or thickness measurements.

The present invention can be useful for autonomous remote monitoring of a subject. The device of the invention can be placed on the skin of a subject, and the presence or absence of one or more markers can be remotely relayed to a heath care worker. Accordingly, the device described herein can include one or more components that would allow for such relay. Exemplary components include an analog-to-digital converter, a radiofrequency module, and/or a telemetry unit (e.g., configured to receive processed data from a data-processing circuit electrically connected to the transducer and to transmit the data wirelessly). In various embodiments, the telemetry unit is fixed within the platform or packaged separately from the platform and connected thereto by a cable.

Multiple Reactions

The present device can be used to perform multiple reactions on-chip. Such reactions can include those to prepare a sample (e.g., to dilute, concentrate, or filter a sample), to bind the sample to a capture agent, to prepare one or more reagents to be reacted with the sample (e.g., to reconstitute a reagent on-chip prior to reacting with the sample), to react the sample with any useful reagent, to store the sample on-chip, and/or to perform other post-processing reactions. To perform multiple reactions, the microneedles, fluidic channels, and transducers can be provided in an array format, such as any described herein.

To allow for multiple reactions or processing steps, the device can include additional chambers in fluidic communication with one or more needles. In one embodiment, the device include one or more mixing chambers in fluidic communication with one or more needles and configured to receive the sample or a portion thereof. The mixing chamber can include one or more reagents (e.g., any described herein), buffers, diluents (e.g., water or saline), salts, etc. Optionally, the mixing chamber can include one or more components to assist in mixing, such as one or more of the following: a bead, a passive mixer, a rotary mixer, a microbubble, an electric field to induce electrokinetic and/or dielectrophoretic flow, a staggered structure to induce chaotic advection, an acoustic mixer, a heater to induce a thermal gradient, and/or a magnetic bead for use with a magnetic field generator.

The device can also include one or more reaction chambers (e.g., to combine one or more reagents (e.g., one or more enzymes and/or beads) within this chamber and/or to incubate reaction mixtures including the sample or a portion thereof), lysing chambers (e.g., to lyse one or more cells within the sample), washing chambers (e.g., to wash one or more components within the sample), elution or extraction chambers (e.g., including one or more filters, particles, beads, sieves, or powders to extract one or more components from the sample), and/or collection chambers (e.g., to collect one or more processed samples or aliquots thereof). In particular embodiments, at least one reaction chamber is in fluidic communication with at least one mixing chamber by a channel. In further embodiments, the reaction chamber is in fluidic communication two or more mixing chambers, thereby combining the substance in each mixing chamber within the reaction chamber. In this manner, parallel or serial sequences of substances can be combined in a controlled manner within a reaction chamber or multiple reaction chambers. A skilled artisan would be able to design arrays of mixing and/or reaction chambers (optionally interconnected with channels) to effect the proper sequence of each reaction step.

Any of the chambers and channels interconnecting such chambers can be surface modified, as described herein. Furthermore, such chambers and channels can include further structures that would be useful for detecting one or more markers. For instance, one or more filters or membranes can be used to separate particular components from the sample and/or the reaction mixture. For instance, when the sample is whole blood, a filter can be used to separate the plasma from other blood components, such as the red blood cells.

Test Samples

The present device can be used to test any useful test sample, such as blood (e.g., whole blood), plasma, serum, transdermal fluid, interstitial fluid, sweat, intraocular fluid, vitreous humor, cerebrospinal fluid, extracellular fluid, lacrimal fluid, saliva, mucus, etc., and any other bodily fluid.

The sample can be obtained from any useful source, such as a subject (e.g., a human or non-human animal), a plant (e.g., an exudate or plant tissue, for any useful testing, such as for genomic and/or pathogen testing), an environment (e.g., a soil, air, and/or water sample), a chemical material, a biological material, or a manufactured product (e.g., such as a food or drug product).

Substances, Including Reagents and Therapeutic Agents

The present device can further be adapted to deliver one or more substances from a reservoir to another region of the device or to a subject. In some embodiments, the device includes one or more reservoirs including a substance for detecting one or more markers of interest. Exemplary substances include a reagent (e.g., any described herein, such as a label, an antibody, a dye, a capture agent, etc.), a buffer, a diluent, a salt, etc.

In other embodiments, the device includes one or more substances that can be injected or delivered to a subject (e.g., one or more therapeutic agents). Such therapeutic substances include, e.g., an analgesic, anesthetic, antiseptic, anticoagulant, drug (e.g. adrenaline and/or insulin), vaccine, medical countermeasure, etc.

Capture Agents

Any useful capture agents can be used in combination with the present invention. The capture agent can directly or indirectly bind the marker of interest. Further, multiple capture agents can be used to bind the marker and provide a detectable signal for such binding. For instance, multiple capture agents are used for a sandwich assay, which requires at least two capture agents and can optionally include a further capture agent that includes a label allowing for detection.

Exemplary capture agents include one or more of the following: a protein that binds to or detects one or more markers (e.g., an antibody or an enzyme), a globulin protein (e.g., bovine serum albumin), a peptide, a nucleotide, a nanoparticle, a microparticle, a sandwich assay reagent, a catalyst (e.g., that reacts with one or more markers), and/or an enzyme (e.g., that reacts with one or more markers, such as any described herein). The capture agent can optionally include one or more labels, e.g. any described herein. In particular embodiments, more than one capture agent, optionally with one or more linking agents, can be used to detect a marker of interest. Furthermore, a capture agent can be used in combination with a label (e.g., any described herein) to detect a maker.

Labels

The present device can include any useful label. The label can be used to directly or indirectly detect a marker. For direct detection, the label is conjugated to a capture agent that binds to the marker. For instance, the capture agent can be an antibody that binds the marker, and the label for direct detection is a nanoparticle attached to the capture agent. For indirect detection, the label is conjugated to a second capture agent that further binds to a first capture agent. A skilled artisan would understand how to optimize combinations of labels, capture agents, and linking agents to detect a marker of interest.

Exemplary labels include one or more fluorescent labels, colorimetric labels, quantum dots, nanoparticles, microparticles, barcodes, radio labels (e.g., RF labels or barcodes), avidin, biotin, tags, dyes, an enzyme that can optionally include one or more linking agents and/or one or more dyes, as well as combinations thereof etc.

Markers, Including Targets

The present device can be used to determine any useful marker or targets. Exemplary markers include one or more physiologically relevant markers, such as glucose, lactate, pH, a protein (e.g., myoglobin, troponin, insulin, or C-reactive protein), an enzyme (e.g., creatine kinase), a catecholamine (e.g., dopamine, epinephrine, or norepinephrine), a cytokine (e.g., TNF-α or interleukins, such as IL-6, IL-12, or IL-1β), an antibody (e.g., immunoglobulins, such as IgA), a biomolecule (e.g., cholesterol or glucose), a neurotransmitter (e.g., acetylcholine, glutamate, dopamine, epinephrine, neuropeptide Y, or norepinephrine), a signaling molecule (e.g., nitric oxide), an antigen (e.g., CD3, CD4, or CD8), an ion (e.g., a cation, such as $K^+$, $Na^+$, $H^+$, or $Ca^{2+}$, or an anion, such as $Cl^-$ or $HCO_3^-$), $CO_2$, $O_2$, $H_2O_2$, a cancer biomarker (e.g., human ferritin, carcinoembryonic antigen (CEA), prostate serum antigen, human chorionic gonadotropin (hCG), *diphtheria antigen*, or C-reactive protein (CRP)), a hormone (e.g., hCG, epinephrine, testosterone, human growth hormone, epinephrine (adrenaline), thyroid hormone (e.g., thyroid-stimulating hormone (TSH), thyroxine (TT4), triiodothyronine (TT3), free thyroxine (FT4), and free triiodothyronine (FT3)), adrenal hormone (e.g., adrenocorticotrophic hormone (ACTH), cortical hormone (F), and 24-hour urine-free cortisol (UFC)), a gonadal hormone (e.g., luteinizing hormone (LH), follicle-stimulating hormone (FSH), testosterone, estradiol (E2), and prolactin (PRL)), cortisol, leptin, or a peptide hormone, such as insulin), an inflammatory marker (e.g., CRP), a disease-state marker (e.g., glycated hemoglobin for diabetes or markers for stress or fatigue), a cardiovascular marker (e.g., CRP, D-dimer, troponin I or T), a blood marker (e.g., hematocrit, or hemoglobin), a cell (e.g., a leukocyte, neutrophil, B-cell, T-cell, lymphocyte, or erythrocyte), a viral marker (e.g., a marker for human immunodeficiency virus, hepatitis, influenza, or *chlamydia*), a metabolite (e.g., glucose, cholesterol, triglyceride, creatinine, lactate, ammonia, ascorbic acid, peroxide, potassium, glutamine, or urea), a nucleic acid (e.g., DNA and/or RNA for detecting one or more alleles, pathogens, single nucleotide polymorphisms, mutations, etc.), an amino acid (e.g., glutamine), a drug (e.g., a diuretic, a steroid, a growth hormone, a stimulant, a narcotic, an opiate, etc.), etc. Other exemplary markers include one or more pathogens, such as *Mycobacterium tuberculosis, Diphtheria antigen, Vibrio cholera, Streptococcus* (e.g., group A), etc.

In particular embodiments, the marker is indicative of exhaustion (e.g., exercise-induced exhaustion) and/or fatigue (e.g., severe fatigue, such as in deployed military personnel). Such markers include, e.g., ACTH, ascorbic acid, CD3, CD4, CD8, CD4/CD8, cholesterol, cortical hormone, cortisol, creatine kinase, E2, epinephrine, FSH, FT3, FT4, glucose, glutamine, glutamate, hematocrit, hemoglobin, human growth hormone, IgA, insulin, insulin-like growth factor, interleukin-6, iron, lactate (e.g., serum or blood lactate), leptin, LH, neuropeptide Y, norepinephrine, peroxide, pH, potassium, PRL, TSH, TT3, TT4, testosterone, and/or urea.

Methods and Use

The present device can be applied for any useful method and/or adapted for any particular use. For instance, point-of-care (POC) diagnostics allow for portable systems, and the device herein can be adapted for POC use. In some embodiments, the device for POC use includes a test sample chamber, a microfluidic processing structure (e.g., any structure described herein, such as a needle, a substrate, and/or a channel), a target recognition region (e.g., including any transducer described herein), an electronic output, a control (e.g., a positive and/or negative controls), and/or a signal transduction region. Exemplary POC devices and uses are described in Gubala V et al., "Point of care diagnostics: status and future," *Anal Chem.* 2012; 84(2):487-515, which is incorporated by reference in its entirety. Such POC devices can be useful for detecting one or more markers for patient care, drug and food safety, pathogen detection, diagnostics, etc.

Wearable sensors are a new paradigm in POC devices, allowing for minimally invasive monitoring of physiological functions and elimination of biological fluid transfer between subject and device; these devices can be capable of providing real-time analysis of a patient's condition. In other embodiments, the device is adapted to include one or more components allowing for a wearable sensor. Exemplary wearable sensors, as well as relevant components, are described in Windmiller J R et al., "Wearable electrochemical sensors and biosensors: A review," *Electroanalysis* 2013; 25:29-46. Such components include a telemetry network including one or more devices (e.g., as described herein), one or more flexible substrates (e.g., where one or more transducers are integrated into a flexible substrate, such as cloth, plastic, or fabric, e.g., Gore-Tex®, an expanded polytetrafluoroethylene (ePTFE), polyimide, polyethylene naphthalate, polyethylene terephthalate, biaxially-oriented polyethylene terephthalate (e.g., Mylar®), or PTFE), and/or one or more flexible electrodes (e.g., a screen printed electrode printed on a flexible substrate, such as any herein).

In some embodiments, the device of the invention is adapted as an epidermal electronic device. Such devices can include, e.g., one or more printed flexible circuits that can be stretched and bent to mimic skin elasticity can perform electrophysiological measurements such as measuring temperature and hydration as well as monitoring electrical signals from brain and muscle activity. Exemplary components for such a device are described in Kim N et al., *Science* 2011; 333:838-43, which is incorporated herein by reference.

In other embodiments, the device of the invention is adapted as a temporary tattoo. Such tattoos can include, e.g., one or more screen printed electrodes directly attached to the skin were recently reported to measure lactate through sweat. Exemplary components for such a device are described Jia W et al., "Electrochemical tattoo biosensors for real-time noninvasive lactate monitoring in human perspiration," *Anal. Chem.* 2013; 85:6553-60, which is incorporated herein by reference.

The device of the invention can be configured for any useful method or treatment. For instance, the device can be configured for locally treating, delivering, or administering a therapeutic substance after detecting one or more markers. Exemplary methods and devices are described in Int. Pub. No. WO 2010/022252, which is incorporated herein by reference.

Kits

The present device can be provided in any useful form, such as in a kit. In some embodiments, the device is provided in combination with an adhesive layer and a backing liner, where peeling of the backing liner exposes the adhesive layer and allows for positioning the device on the skin of a subject. In other embodiments, the kit includes a device (e.g., any described herein), an instruction for use, and, optionally, one or more therapeutic agent (e.g., any described herein).

Packaged Chip

The present device can be provided in any useful package. For instance, such a package can include a packaged chip having a housing for the device of the invention. In one embodiment, the housing includes a substantially planar substrate having an upper surface and an opposing lower surface; a first fluidic opening disposed on the upper surface of the substrate; a second fluidic opening disposed on the lower surface of the substrate; a first fluidic channel fluidically connecting the first fluidic opening to the second fluidic opening; and a first adhesive layer adhered to the upper surface, having a hole disposed through the layer, wherein the hole is substantially aligned with, and fluidically coupled to, the first fluidic opening in the substrate. In some embodiments, the housing includes one or more structures allowing for integrating with a fluidic printed wiring board having a standard electrical printed circuit board and one or more fluidic channels embedded inside the board. An exemplary packaged chip is provided in U.S. Pat. No. 6,548,895, which is incorporated by reference in its entirety. Further components for a packaged chip include a substrate including an electrically insulating material, one or more electrical leads, a substantially planar base, an external fixture, etc., as well as any other components described in U.S. Pat. Nos. 6,443,179 and 6,548,895, each of which is incorporated herein by reference in its entirety.

The device of the invention can be provided in any useful format. For instance, the device can be provided with particular components integrated into one package or monolithic structure. A non-limiting example of such an integrated device is provided in FIG. 1A, where the needles, fluidics, and electrode array are provided in an integrated format. In other examples, the device is provided as a modular package, in which the needles, fluidics, and electrodes are provided as separate plug-and-play modules that can be combined. In particular embodiments, a sensor module includes a packet of electrode arrays with each packet containing specific chemistries. In further embodiments, the sensor module is configured to be relevant for the desired analyte, such as to detect a particular drug or a particular virus. Further modules can include a needle module including one or more needles (e.g., an array of needles); a fluidics module including one or more chambers, valves, and/or channels; a delivery module including one or more therapeutic agents; and/or a reagent module including one or more prepackaged reagents and buffers configured for a particular test or analyte. Such modules can be reusable or disposable. For instance, if the sample processing is extensive, one would want a reusable fluidics module, which is configured for fluidic communication with the needle module and sensor module. In further embodiments, the needle and sensor modules can be disposable. In another example, if sample processing or sensing requires an elaborate needle (e.g., a needle having a particular geometrical configuration and/or surface modification), then the needle module can be configured to be reusable. Other considerations include possibility of contamination of one or more modules, etc. A skilled artisan would understand how modules can be configured for fluidic communication with other modules and designed for reusability or disposability.

EXAMPLE

Example 1: Diagnostic/Drug Delivery "Sense-Respond" Device

We describe the development of a compact system that simultaneously measures the systemic physiological state of an individual and can appropriately inject drugs (e.g., adrenaline, insulin, analgesia, medical counter measures, etc.), thereby creating a "Sense-Respond" platform to monitor health, improve human performance, and treat diseases and/or exposure to chemical and/or biological threats. A wearable transdermal diagnostic/drug delivery device capable of interfacing with an individual would enable continually monitoring and maintaining individual health over extended periods and the ability to treat diseases, improve athletic performance, as well as enable full situational awareness for a warfighter in the field. This need arises from the lack of autonomous and portable diagnostic platforms available for remote monitoring and the need to use this information to intelligently inject drugs and/or medical countermeasures.

The device can include a sensor component and an electronic component. The sensor component can include a microfluidic device, based on microneedles, which can be worn on an individual and can painlessly access biological fluid (e.g., blood and/or interstitial fluid) through the skin for real-time, long-term autonomous diagnostics of health and fitness. The electronic component can include one or more electronic circuitry. This electronic component can be integrated with the sensor component on a single platform, thereby realizing an on-body microneedle diagnostic/drug delivery device. In particular embodiments, the electronic component is configured to provide an electronic feedback loop between sensing needles and drug delivery needles on the same platform.

We previously tailored hollow polymeric microneedles for the ex vivo detection of ascorbic acid and peroxide, potassium, and the simultaneous detection of glucose, lactate, and pH (Miller P R et al., "Integrated carbon fiber electrodes within hollow polymer microneedles for transdermal electrochemical sensing," *Biomicrofluidics* 2011; 5:013415 (14 pages); Windmiller J R et al., "Bicomponent microneedle array biosensor for minimally-invasive glutamate monitoring," *Electroanalysis* 2011; 23(10):2302-9; and Miller P R et al., "Multiplexed microneedle-based biosensor array for characterization of metabolic acidosis," *Talanta* 2012; 88:739-42, each of which is incorporated by reference in its entirety). The electrode transducers in these cases were placed either inside or directly underneath the microneedles, a configuration considered unamenable for multiple and/or long-term extractions in vivo.

Figure 1B:
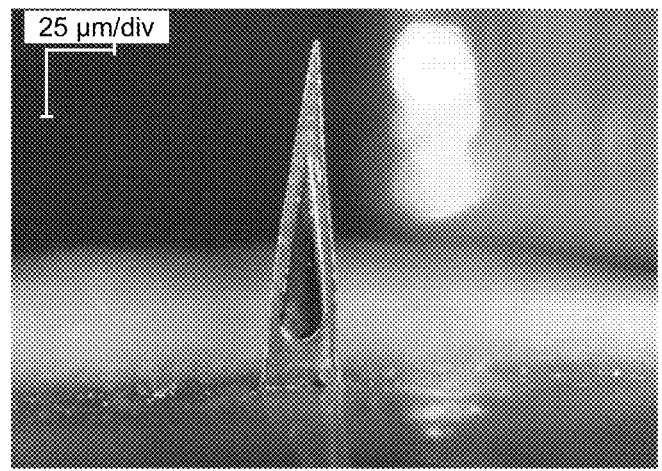

To circumvent these problems, we describe a microneedle device that can extract interstitial fluid for analysis over downstream electrode arrays (FIG. 1A). The device includes a 3×3 array of microneedles, which is connected fluidically to a fluidic channel. An exemplary microneedle is provided in FIG. 1B. In addition, the channel provides fluidic communication between the microneedle(s) and the electrode array. As can be seen in FIG. 1A, the device includes an array of ten electrodes, of which eight are working electrodes and two are reference and counter electrodes.

The device can be configured to detect and monitor any useful physiological condition, disease state, or health, as well as biomarkers or physiological parameters related to such conditions. For example, exercise-induced exhaustion without adequate rest is damaging to a person's health and performance. Even for elite athletes overexertion can result in impaired performance for weeks to years. Little data is available concerning biomarkers of extreme fatigue for military personnel, particularly in deployment conditions. Exercise physiological studies as well as studies looking at biomarkers in the blood of military personnel involved in intense training exercises have identified cortisol, glutamine, glutamate, serum lactate, interleukin-6, testosterone, thyroid hormones, human growth hormone, insulin and glucose, adrenaline, and neuropeptide Y (NPY) as important biomarkers for overtraining syndrome and fatigue (see, e.g., Wyatt F B et al., "The overtraining syndrome: A meta-analytic review," *J. Exerc. Physiol.* 2013 April; 16(2):12-23; Weeks S R et al., "Physiological and psychological fatigue in extreme conditions: the military example," *PM & R* 2010 May; 2(5):438-4; Purvis D et al., "Physiological and psychological fatigue in extreme conditions: overtraining and elite athletes," *PM & R* 2010 May; 2(5):442-50; and Li X et al., "Experimental study on neuroendocrinological and immunological characteristics of the military-trained artillerymen," *Chin. Med. J.* (Engl.) 2012 April; 125(7):1292-6). Thus, the present invention includes systems and devices configured to detect any of these biomarkers.

Furthermore, the devices of the invention can be employed for monitoring purposes, as well as training and clinical study tools. For example, mechanisms underlying fatigue, performance, and stress are complicated. In addition, more information is needed regarding detectable markers correlated with such mechanisms. In one instance, fatigue associated with combat simulations also result in increased resting levels of oxygen consumption and increased production of adrenaline and NPY. NPY increases adrenaline production, decreases anxiety, and enhances memory and attention. The combination of adrenaline and NPY production enhances performance, even under stress conditions (Weeks S R et al., "Physiological and psychological fatigue in extreme conditions: the military example," *PM & R* 2010 May; 2(5):438-4). However, it is unknown how long this high level of performance can be maintained. It is noteworthy that military personnel receiving uncharacteristically rigorous training, such as Special Forces, return to basal levels of biomarkers much more quickly than their peers who have not had the same level of training. Therefore, the sensing/drug delivery system proposed here can be used as both a training tool as well as an important mission asset to help determine the health status of a warfighter and improve human performance. Furthermore, the devices and systems of the invention can also be used for athletes, and to monitor and improve healthcare for any individual.

Device Components

The components of the biosensor/drug delivery unit are based on the microneedle array foundation and include (i) a sensor component including a microneedle array and an electrochemical sensor array; (ii) a delivery component including a microneedle array and one or more depots (e.g., reservoirs or chambers) containing therapeutic agent(s); (iii) a fluidic component, optionally including pumps, valves, and vacuum sources; and (iv) an electronic component including a printed wiring assembly with power (FIG. 2). All components can be integrated into a single unit packaged unit.

As shown in FIG. 2, the microneedle array can be divided into several groups, e.g., one for acquisition of interstitial fluid (three needles on left side of array in FIG. 2) and one group for each of the desired therapeutic agents to be delivered (two needles on right side of array in FIG. 2). In this way, the system is scalable and customizable to accommodate a variety of analytes for a unique environment. Another needle (between the two groups) can be included to return or re-inject analyzed interstitial fluid back into the subject.

The groups of microneedles can be isolated from each other on the opposite side of the microneedle array using microfluidic chambers. These can be fabricated using laminate, 3D printing methods, standard CMOS fabrication, etc. Alternatively, traditional machining and MEMS fabrication methods can be used. Optionally, the upper wall of the microfluidic chambers can include a printed wiring circuit board. In an alternative embodiment, the upper wall can include a polymeric coating that protects the printed wiring circuit board and the electrochemical sensor array from contaminants (e.g., a protein, such as albumin) that bind to sensitive electronic components.

The device can include one or more sensor arrays in fluidic communication with the microneedle(s). The sensor (e.g., an electrochemical (e-chem) sensor array) can include electrodes of various materials, some of which can be modified with appropriate chemistry and capture agents to achieve specific sensing of target markers and analytes. As shown in FIG. 2, these electrodes can be located on one side of the printed circuit board. These electrodes can use electrical vias to route signals to the circuitry on the other side of the printed circuit board.

The device can include a plurality of chambers or wells containing various drugs and therapeutic agents. In particular embodiments, such chambers can be provided in replicates, which will allow for varying the dose of the selected agent. The selected agent with its appropriate quantity can be delivered by actuating one or more pumps (e.g., thermal pumps) and/or valves (e.g., membrane valves, such as hydrophobic forms thereof). The process can then be repeated to sense the biomarker concentration response due to the delivered agent. Status lights (e.g., LED indicators) can be updated to reflect detected concentrations and quantity of agent delivered.

The printed circuit board (PCB) serves two general functions. First, the PCB provides circuitry configured to receive input electrical signals from the sensor array. Second, the PCB is configured to provide output electrical signals to one or more depots containing therapeutic agents. In this way, detected biomarkers control whether the subject will be treated (or re-treated) with the therapeutic agent. Of course, the PCB can include various other circuitry and components to perform other functions, such as algorithms to process input and output signals, communication circuitry to communicate between components on the PCB or between the PCB and an external unit, and/or power circuitry to provide power to one or more components in the system (e.g., one or more heaters, pumps, valves, circuitry, etc.).

In one embodiment, on the same side of the circuit board as the electrochemical sensor array will be resistive elements (e.g., as seen in FIG. 2, the electrochemical sensor array and resistive element are both on the bottom side of the PCB). Resistive elements can be used to heat fluids in the drug delivery reservoirs and/or to generate pressure large enough to overcome the hydrophobic barrier of the membrane valve and drive the drug solution into the interstitial space. Alternatively, different pumping components can be integrated.

On the opposite side of the circuit board, the electronic components can be located (e.g., as seen in FIG. 2, electronic components are on the top side of the PCB). Various electronic components can be included. In one embodiment, a battery source as well as a microprocessor, vacuum pump, and LED indicators will be the major components. In yet another embodiment, one or more electronic components can be potted (e.g., with a potting material, such as an adhesive, a polymer, etc., such as any herein) to provide a robust mechanical package and a surface to which the device can be mounted to a tape or other fabric for securing it to the target site.

Figure 3:
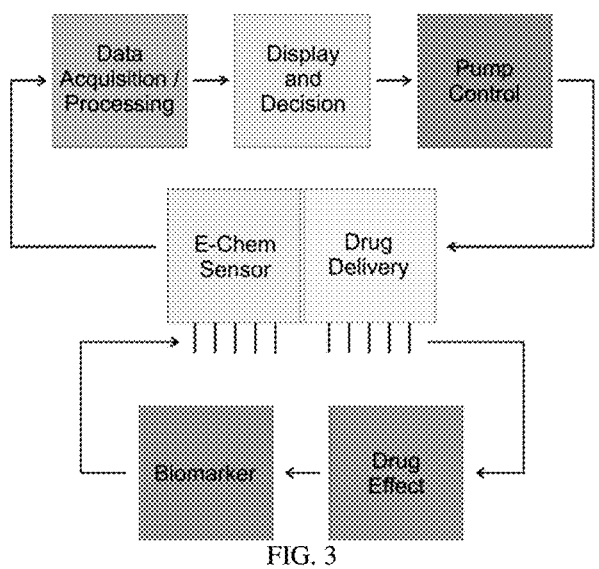
FIG. 3 provides a block diagram of an exemplary operational process for detecting, monitoring, and/or treating a user with a system of the invention.

FIG. 3 provides an exemplary block diagram of a proposed operational process. Starting with the block labeled "Biomarker," the body produces a biomarker in response to a particular condition of interest, which concentration is then detected by the electrochemical sensor array (block labeled "E-Chem Sensor"). The microneedle array acquires the sample either through passive diffusion or through actuation of a pump to acquire a larger volume of sample. The data is acquired, processed, and a decision is made by on-device circuitry and programmed algorithms (blocks labeled "Data Acquisition/Processing," "Display and Decision," and "Pump Control"). If a therapeutic agent is required, then a signal is transmitted to the drug delivery chambers and associated microneedles (block labeled "Drug Delivery"). After delivery, interstitial fluid can be re-sampled with re-tested to determine the effect of the dosing, timing, and type of drug (block labeled "Drug Effect"). For re-sampling and testing, the operational process can be repeated at any useful time point(s) (starting from block labeled "Biomarker").

These processes can be communicated to the user in any useful manner. For instance, the algorithm can include one or more communication signals, which activate one or more indicators (e.g., LED indicators) to communicate sensor and drug delivery states to the user.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A device for detecting one or more markers in a sample from a target site of a subject, the device comprising:
   (i) a sensor component comprising at least one first hollow needle and at least one first sensing transducer in fluidic communication with the at least one first hollow needle, wherein the at least one first sensing transducer is configured to detect one or more markers in the sample;
   (ii) a delivery component comprising one or more depots configured to contain one or more therapeutic agents;
   (iii) a return needle configured to return fluid to the target site of the subject;
   (iv) an electronic component comprising circuitry configured for signal processing, signal control, power control, and/or communication signaling, wherein the electronic component is connected electrically to the sensor and delivery components.

2. The device of claim 1, wherein (i) the sensor component comprises:
   a plurality of hollow needles, wherein each needle has an interior surface facing the hollow lumen and an exterior surface, the distal end of the exterior surface for at least one needle comprises a puncturing edge, and at least one needle has a length of more than about 0.5 mm;
   a substrate coupled to the plurality of hollow needles, wherein the substrate comprises one or more inlets in fluidic communication with the proximal end of at least one needle; and
   a first channel disposed within the substrate and in fluidic communication with at least one inlet of the substrate; and
   wherein the at least one first sensing transducer is in fluidic communication with the first channel.

3. The device of claim 1, wherein (ii) the delivery component further comprises:
   a plurality of second hollow needles, wherein each second hollow needle has an interior surface facing the hollow lumen and an exterior surface, the distal end of the exterior surface for at least one second hollow needle comprises a puncturing edge, and at least one second hollow needle has a length of more than about 0.5 mm; and wherein at least one second hollow needle is in fluidic communication with at least one depot.

4. The device of claim 3, further comprising one or more pumps and/or valves in fluidic communication with the one or more depots.

5. The device of claim 1, wherein (iv) the electronic component comprises a battery, a pump fluidically connected to at least one first hollow needle of the sensor component, and an electrical connection to one or more indicators.

6. The device of claim 1, further comprising (v) a fluidic component comprising one or more fluidic channels, chambers, pumps, and/or valves configured to provide fluidic communication between the sensor or delivery component and the sample.

7. The device of claim 2, wherein the substrate comprises a further inlet in fluidic communication with a proximal end of the return needle.

8. The device of claim 7, further comprising a pump in fluidic communication with the further inlet of the substrate.

9. The device of claim 1, wherein the at least one first hollow needle is configured to obtain the sample from a subject.

10. The device of claim 9, wherein a puncturing edge of the first hollow needle comprises a tapered point, a sharpened bevel, or one or more prongs.

11. The device of claim 1, wherein the at least one first hollow needle comprises a polymer, a metal, silicon, glass, a composite material, or a combination thereof.

12. The device of claim 1, wherein the at least one first sensing transducer is selected from the group consisting of an electrode, an ion selective electrode, an optical sensor, an array of any of these, and combinations thereof.

13. The device of claim 12, wherein the at least one first sensing transducer further comprises a modified surface.

14. The device of claim 12, wherein at least one first sensing transducer is an electrode selected from the group of a planar electrode, a three-dimensional electrode, a porous electrode, a microelectrode, and a nanoelectrode, or an array thereof.

15. The device of claim 1, wherein the sensor component, delivery component, the return needle, and electronic component are configured into an integrated structure.

16. The device of claim 1, wherein the sensor component, delivery component, and electronic component are configured into separate modules.

17. The device of claim 1, wherein the at least one first hollow needle is configured to obtain an interstitial fluid in vivo.

18. A kit comprising:
   (i) a device of claim 1; and
   (ii) a therapeutic agent configured to be injected into the depot.

19. The kit of claim 18, wherein the agent is selected from the group consisting of an anesthetic, an antiseptic, an anticoagulant, a drug, and a vaccine.

20. A method of monitoring one or more markers from a target site of a subject, the method comprising:
   (i) affixing the device of claim 1 on the target site of the subject;
   (ii) activating the device, thereby monitoring one or more markers in the target site; and
   (iii) returning fluid to the target site of the subject by employing the return needle.

21. The method of claim 20, further comprising (iv) delivering one or more therapeutic agents to the subject.

22. The method of claim 20, wherein the sample is interstitial fluid, blood, plasma, serum, transdermal fluid, sweat, or a bodily fluid.

* * * * *